(12) United States Patent
Chan et al.

(10) Patent No.: US 9,314,284 B2
(45) Date of Patent: Apr. 19, 2016

(54) HIGHLY-VERSATILE VARIABLE-ANGLE BONE PLATE SYSTEM

(71) Applicant: DePuy Synthes Products, Inc., Raynham, MA (US)

(72) Inventors: Jason S. Chan, Dresher, PA (US); Alberto A. Fernandez, Montevideo (UY)

(73) Assignee: DePuy Synthes Products, Inc., Raynham, MA (US)

( * ) Notice: Subject to any disclaimer, the term of this patent is extended or adjusted under 35 U.S.C. 154(b) by 149 days.

(21) Appl. No.: 14/056,240

(22) Filed: Oct. 17, 2013

(65) Prior Publication Data

US 2014/0180345 A1 Jun. 26, 2014

Related U.S. Application Data

(63) Continuation of application No. 11/971,358, filed on Jan. 9, 2008, now Pat. No. 8,574,268, and a continuation-in-part of application No. 10/763,689, filed on Jan. 26, 2004, now Pat. No. 7,637,928.

(60) Provisional application No. 60/955,506, filed on Aug. 13, 2007.

(51) Int. Cl.
*A61B 17/80* (2006.01)
*A61B 17/17* (2006.01)
(Continued)

(52) U.S. Cl.
CPC ......... *A61B 17/8057* (2013.01); *A61B 17/1728* (2013.01); *A61B 17/8605* (2013.01);
(Continued)

(58) Field of Classification Search
CPC . A61B 17/80; A61B 17/8057; A61B 17/1728

USPC .................................. 606/280–331; 411/380
See application file for complete search history.

(56) References Cited

U.S. PATENT DOCUMENTS

| 1,203,546 A | 10/1916 | Parsons |
| 2,228,584 A | 1/1941 | Place |

(Continued)

FOREIGN PATENT DOCUMENTS

| CA | 1112803 | 11/1981 |
| CH | 611147 | 5/1979 |

(Continued)

OTHER PUBLICATIONS

ACE Symmetry, "Curves in All the Right Places", 1996, 3 pages.
(Continued)

*Primary Examiner* — Christopher Beccia
(74) *Attorney, Agent, or Firm* — Baker & Hostetler LLP

(57) ABSTRACT

A bone plate system for internal fixation of bone fractures includes a bone plate having a plurality of bone plate holes. The holes are constructed to receive either a non-locking, locking, or variable-angle locking bone screw. The holes have discrete columns of teeth or thread segments arranged around the inner surface of the hole for engaging threads on the heads of locking and variable-angle locking bone screws. Conventional locking bone screws engage the bone plate coaxially with the central axis of the bone plate hole. Variable-angle locking bone screws can engage the bone plate at a selectable angle within a range of selectable angles relative to the central axis of the bone plate hole. The head of the variable-angle locking screw is at least partially spherical, and the thread thereon has a profile that follows the arc-shaped radius of curvature of the spherical portion of the screwhead.

19 Claims, 36 Drawing Sheets

(51) Int. Cl.
*A61B 17/86* (2006.01)
*A61B 19/00* (2006.01)

(52) U.S. Cl.
CPC .......... *A61B17/8061* (2013.01); *A61B 17/864* (2013.01); *A61B 2017/1782* (2013.01); *A61B 2019/462* (2013.01); *A61B 2019/467* (2013.01)

(56) References Cited

U.S. PATENT DOCUMENTS

| | | | |
|---|---|---|---|
| 2,443,363 A | 6/1948 | Townsend et al. | |
| 2,477,430 A | 7/1949 | Swanstrom | |
| 2,846,701 A | 8/1958 | Bedford | |
| 3,229,743 A | 1/1966 | Derby | |
| 3,263,949 A | 8/1966 | Conrad | |
| 3,314,326 A | 4/1967 | Bedford | |
| 3,364,807 A | 1/1968 | Holton | |
| 3,388,732 A | 6/1968 | Holton | |
| 3,463,148 A | 8/1969 | Treace | |
| 3,551,389 A | 12/1970 | Prince, Jr. | |
| 3,552,389 A | 1/1971 | Allgower et al. | |
| 3,630,261 A | 12/1971 | Gley | |
| 3,688,972 A | 9/1972 | Allgower et al. | |
| 3,695,618 A | 10/1972 | Woolley et al. | |
| 3,716,050 A | 2/1973 | Johnston | |
| 3,741,205 A | 6/1973 | Markolf et al. | |
| 3,744,488 A | 7/1973 | Cox | |
| 3,779,240 A | 12/1973 | Kondo | |
| 3,877,339 A | 4/1975 | Muenchinger | |
| RE28,841 E | 6/1976 | Allgower et al. | |
| 3,967,049 A | 6/1976 | Brandt | |
| 3,996,834 A | 12/1976 | Reynolds | |
| 4,029,091 A | 6/1977 | Von Bezold et al. | |
| 4,175,555 A | 11/1979 | Herbert | |
| 4,219,015 A | 8/1980 | Steinemann | |
| 4,263,904 A | 4/1981 | Judet | |
| 4,304,039 A | 12/1981 | Asmus | |
| 4,338,926 A | 7/1982 | Kummer et al. | |
| 4,355,198 A | 10/1982 | Gartland, Jr. | |
| 4,408,601 A | 10/1983 | Wenk | |
| 4,429,690 A | 2/1984 | Angelino-Pievani | |
| RE31,628 E | 7/1984 | Allgower et al. | |
| 4,484,570 A | 11/1984 | Sutter et al. | |
| 4,491,317 A | 1/1985 | Bansal | |
| 4,493,317 A | 1/1985 | Klaue | |
| 4,513,744 A | 4/1985 | Klaue | |
| 4,565,193 A | 1/1986 | Streli | |
| 4,580,225 A | 4/1986 | Thompson | |
| 4,612,923 A | 9/1986 | Kronenthal | |
| 4,630,985 A | 12/1986 | Simons | |
| 4,651,724 A | 3/1987 | Berentey et al. | |
| 4,683,878 A | 8/1987 | Carter | |
| 4,717,613 A | 1/1988 | Ottaviano | |
| 4,776,329 A | 10/1988 | Treharne | |
| 4,781,183 A | 11/1988 | Casey et al. | |
| 4,794,918 A | 1/1989 | Wolter | |
| 4,838,252 A | 6/1989 | Klau | |
| 4,858,601 A | 8/1989 | Glisson | |
| 4,867,144 A | 9/1989 | Karas et al. | |
| 4,927,421 A | 5/1990 | Goble et al. | |
| 4,957,497 A | 9/1990 | Hoogland et al. | |
| 4,988,350 A | 1/1991 | Herzberg | |
| 5,002,544 A | 3/1991 | Klaue et al. | |
| 5,006,120 A | 4/1991 | Carter | |
| 5,027,904 A | 7/1991 | Miller et al. | |
| 5,039,265 A | 8/1991 | Rath et al. | |
| 5,041,113 A | 8/1991 | Biedermann et al. | |
| 5,041,114 A | 8/1991 | Chapman et al. | |
| 5,053,036 A | 10/1991 | Perren et al. | |
| 5,085,660 A | 2/1992 | Lin | |
| 5,108,399 A | 4/1992 | Eitenmuller et al. | |
| 5,129,901 A | 7/1992 | Decoste | |
| 5,147,361 A | 9/1992 | Ojima et al. | |
| 5,151,103 A | 9/1992 | Tepic et al. | |
| 5,190,544 A | 3/1993 | Chapman et al. | |
| 5,197,966 A | 3/1993 | Sommerkamp | |
| 5,261,910 A | 11/1993 | Warden et al. | |
| 5,269,784 A | 12/1993 | Mast | |
| 5,275,601 A | 1/1994 | Gogolewski et al. | |
| 5,304,180 A | 4/1994 | Slocum | |
| 5,306,275 A | 4/1994 | Bryan | |
| 5,324,290 A | 6/1994 | Zdeblick et al. | |
| 5,336,224 A | 8/1994 | Selman | |
| 5,360,448 A | 11/1994 | Thramann | |
| 5,364,398 A | 11/1994 | Chapman et al. | |
| 5,364,399 A | 11/1994 | Lowery et al. | |
| 5,403,136 A * | 4/1995 | Mathys | 411/310 |
| 5,429,641 A | 7/1995 | Gotfried | |
| 5,514,138 A | 5/1996 | McCarthy | |
| 5,534,032 A | 7/1996 | Hodorek | |
| 5,558,674 A | 9/1996 | Heggeness et al. | |
| 5,571,198 A | 11/1996 | Drucker et al. | |
| 5,591,168 A | 1/1997 | Judet et al. | |
| 5,601,551 A | 2/1997 | Taylor et al. | |
| 5,601,553 A | 2/1997 | Trebing et al. | |
| 5,607,426 A | 3/1997 | Ralph et al. | |
| 5,607,428 A | 3/1997 | Lin | |
| 5,620,445 A | 4/1997 | Brosnahan et al. | |
| 5,674,222 A | 10/1997 | Berger et al. | |
| 5,702,399 A | 12/1997 | Kilpela et al. | |
| 5,709,686 A | 1/1998 | Talos et al. | |
| 5,741,258 A | 4/1998 | Klaue et al. | |
| 5,749,872 A | 5/1998 | Kyle et al. | |
| 5,772,662 A | 6/1998 | Chapman et al. | |
| 5,785,713 A | 7/1998 | Jobe | |
| 5,810,823 A | 9/1998 | Klaue et al. | |
| 5,938,664 A | 8/1999 | Winquist et al. | |
| 5,954,722 A | 9/1999 | Bono | |
| 5,961,524 A | 10/1999 | Crombie | |
| 5,968,047 A | 10/1999 | Reed | |
| 5,976,141 A | 11/1999 | Haag et al. | |
| 5,999,940 A | 12/1999 | Ranger | |
| 6,001,099 A | 12/1999 | Huebner | |
| 6,022,352 A | 2/2000 | Vandewalle | |
| 6,030,162 A | 2/2000 | Huebner | |
| 6,030,389 A | 2/2000 | Wagner et al. | |
| 6,096,040 A | 8/2000 | Esser | |
| 6,129,730 A | 10/2000 | Bono et al. | |
| 6,152,927 A | 11/2000 | Farris et al. | |
| 6,183,475 B1 | 2/2001 | Lester et al. | |
| 6,206,881 B1 | 3/2001 | Frigg et al. | |
| 6,228,085 B1 | 5/2001 | Theken et al. | |
| 6,261,291 B1 | 7/2001 | Talaber et al. | |
| 6,306,136 B1 | 10/2001 | Baccelli | |
| 6,322,562 B1 | 11/2001 | Wolter | |
| 6,342,055 B1 | 1/2002 | Eisermann et al. | |
| 6,348,052 B1 | 2/2002 | Sammarco | |
| 6,364,882 B1 | 4/2002 | Orbay | |
| 6,423,064 B1 | 7/2002 | Kluger | |
| 6,440,135 B2 | 8/2002 | Orbay et al. | |
| 6,454,769 B2 | 9/2002 | Wagner et al. | |
| 6,454,770 B1 | 9/2002 | Klaue | |
| 6,468,278 B1 | 10/2002 | Muckter | |
| 6,527,776 B1 | 3/2003 | Michelson | |
| 6,565,525 B1 | 5/2003 | Burbank et al. | |
| 6,565,569 B1 | 5/2003 | Assaker et al. | |
| 6,575,975 B2 | 6/2003 | Brace et al. | |
| D479,331 S | 9/2003 | Pike et al. | |
| 6,623,486 B1 | 9/2003 | Weaver et al. | |
| 6,669,701 B2 | 12/2003 | Steiner et al. | |
| 6,719,759 B2 | 4/2004 | Wagner et al. | |
| 6,730,091 B1 | 5/2004 | Pfefferle et al. | |
| 6,893,443 B2 | 5/2005 | Frigg et al. | |
| 6,955,677 B2 | 10/2005 | Dahners | |
| 6,974,461 B1 | 12/2005 | Wolter | |
| 7,044,953 B2 | 5/2006 | Capanni | |
| 7,128,744 B2 | 10/2006 | Weaver et al. | |
| 7,179,260 B2 | 2/2007 | Gerlach et al. | |
| 7,309,340 B2 | 12/2007 | Fallin et al. | |
| 7,338,491 B2 | 3/2008 | Baker et al. | |
| 7,341,589 B2 | 3/2008 | Weaver et al. | |
| 7,354,441 B2 | 4/2008 | Frigg | |
| 7,537,596 B2 | 5/2009 | Jensen | |
| 7,695,502 B2 | 4/2010 | Orbay et al. | |

(56) References Cited

U.S. PATENT DOCUMENTS

| | | |
|---|---|---|
| 7,766,916 B2 | 8/2010 | Leyden et al. |
| 8,075,561 B2 | 12/2011 | Wolter |
| 8,118,846 B2 | 2/2012 | Leither et al. |
| 8,343,196 B2 | 1/2013 | Schneider |
| 2002/0156474 A1 | 10/2002 | Wack et al. |
| 2004/0073218 A1 | 4/2004 | Dahners |
| 2004/0260306 A1 | 12/2004 | Fallin et al. |
| 2005/0015089 A1 | 1/2005 | Young et al. |
| 2005/0107796 A1 | 5/2005 | Gerlach et al. |
| 2005/0165400 A1 | 7/2005 | Fernandez |
| 2005/0261688 A1 | 11/2005 | Grady et al. |
| 2005/0277937 A1* | 12/2005 | Leung et al. ............ 606/69 |
| 2006/0004361 A1 | 1/2006 | Hayeck et al. |
| 2006/0217722 A1 | 9/2006 | Dutoit et al. |
| 2006/0235400 A1 | 10/2006 | Schneider |
| 2007/0016205 A1 | 1/2007 | Beutter et al. |
| 2007/0083207 A1 | 4/2007 | Ziolo et al. |
| 2007/0088360 A1 | 4/2007 | Orbay et al. |
| 2007/0162016 A1 | 7/2007 | Matityahu |
| 2007/0206244 A1 | 9/2007 | Kobayashi |
| 2007/0260244 A1 | 11/2007 | Wolter |
| 2008/0140130 A1 | 6/2008 | Chan et al. |
| 2008/0208259 A1 | 8/2008 | Gilbert et al. |
| 2008/0234749 A1 | 9/2008 | Forstein |
| 2008/0300637 A1 | 12/2008 | Austin et al. |
| 2009/0018557 A1 | 1/2009 | Pisharodi |
| 2009/0018588 A1 | 1/2009 | Eckhof et al. |
| 2009/0076553 A1 | 3/2009 | Wolter |
| 2009/0076554 A1 | 3/2009 | Huebner et al. |
| 2009/0118768 A1 | 5/2009 | Sixto et al. |
| 2009/0143824 A1 | 6/2009 | Austin et al. |
| 2009/0143825 A1 | 6/2009 | Graham et al. |
| 2009/0292318 A1 | 11/2009 | White et al. |
| 2009/0312803 A1 | 12/2009 | Austin et al. |
| 2010/0016858 A1 | 1/2010 | Michel |
| 2010/0030277 A1 | 2/2010 | Haidukewych et al. |
| 2010/0057086 A1 | 3/2010 | Price et al. |
| 2010/0076496 A1 | 3/2010 | Fernandez |
| 2010/0094357 A1 | 4/2010 | Wallenstein et al. |
| 2010/0100134 A1 | 4/2010 | Mocanu |
| 2010/0137919 A1 | 6/2010 | Wolter |
| 2010/0274296 A1 | 10/2010 | Appenzeller et al. |
| 2010/0312286 A1 | 12/2010 | Dell'Oca |
| 2011/0224671 A1 | 9/2011 | Koay et al. |
| 2013/0116735 A1 | 5/2013 | Schneider |
| 2013/0190828 A1 | 7/2013 | Schneider |
| 2013/0197589 A1 | 8/2013 | Schneider |

FOREIGN PATENT DOCUMENTS

| | | |
|---|---|---|
| CH | 672245 | 11/1989 |
| CH | 675531 | 10/1990 |
| DE | 3442004 | 4/1986 |
| DE | 4341980 | 6/1995 |
| DE | 4343117 | 6/1995 |
| DE | 4438264 | 3/1996 |
| DE | 19629011 | 1/1998 |
| DE | 9321544 | 9/1999 |
| DE | 19832513 | 2/2000 |
| DE | 20309361 | 9/2003 |
| DE | 20317651 | 3/2004 |
| DE | 10 2005/04276 | 1/2007 |
| EP | 0053999 | 6/1982 |
| EP | 158030 | 10/1985 |
| EP | 0207884 | 1/1987 |
| EP | 241914 | 10/1987 |
| EP | 0266146 | 5/1988 |
| EP | 0360139 | 3/1990 |
| EP | 0410309 | 1/1991 |
| EP | 0515828 | 12/1992 |
| EP | 0530585 | 3/1993 |
| EP | 0848600 | 6/1998 |
| EP | 1468655 | 10/2004 |
| EP | 1604619 | 12/2005 |
| EP | 1658015 | 5/2006 |
| EP | 1712197 | 10/2006 |
| EP | 1741397 | 1/2007 |
| EP | 1767160 | 3/2007 |
| FR | 742618 | 3/1933 |
| FR | 2233973 | 1/1975 |
| FR | 2405062 | 6/1979 |
| FR | 2405705 | 6/1979 |
| FR | 2405706 | 6/1979 |
| FR | 2496429 | 6/1982 |
| FR | 2674118 | 9/1992 |
| GB | 997733 | 7/1965 |
| GB | 1237405 | 6/1971 |
| GB | 1250413 | 10/1971 |
| GB | 1312189 | 4/1973 |
| GB | 1385398 | 2/1975 |
| GB | 1575194 | 9/1980 |
| JP | 11299804 | 8/1999 |
| JP | 11512004 | 10/1999 |
| JP | 2001/525701 | 12/2001 |
| JP | 2001/525702 | 12/2001 |
| JP | 2002/232185 | 8/2002 |
| JP | 2002/542875 | 12/2002 |
| JP | 2003/509107 | 3/2003 |
| SU | 1037911 | 8/1983 |
| SU | 1279626 | 12/1986 |
| WO | WO 87/00419 | 1/1987 |
| WO | WO 87/06982 | 11/1987 |
| WO | WO 88/03781 | 6/1988 |
| WO | WO 96/29948 | 10/1996 |
| WO | WO 97/09000 | 3/1997 |
| WO | WO 98/51226 | 11/1998 |
| WO | WO 00/53110 | 9/2000 |
| WO | WO 00/53111 | 9/2000 |
| WO | WO 00/66012 | 11/2000 |
| WO | WO 01/19267 | 3/2001 |
| WO | WO 01/54601 | 8/2001 |
| WO | WO 02/096309 | 12/2002 |
| WO | WO 2004/089233 | 10/2004 |
| WO | WO 2005/018472 | 3/2005 |
| WO | WO 2007/014279 | 2/2007 |
| WO | WO 2007/108734 | 9/2007 |
| WO | WO 2009/023666 | 2/2009 |
| WO | WO 2009/058969 | 5/2009 |

OTHER PUBLICATIONS

"Cone Drive History and Double Enveloping Technology", http://conedrive.com/products, retrieved Apr. 20, 2006.

European Patent Application No. 12006606.3: Extended European Search Report dated Jan. 21, 2013, 7 pages.

European Patent Application No. 12006615.4: Extended European Search Report dated Jan. 21, 2013, 7 pages.

European Patent Application No. 12006617.0: Extended European Search Report dated Jan. 21, 2013, 8 pages.

International Patent Application No. PCT/CH03/00577: International Search Report dated Apr. 28, 2004, 4 pages.

International Patent Application No. PCT/CH03/00577: International Search Report dated Apr. 28, 2004, 3 pages.

International Patent Application No. PCT/US2008/072894: International Search Report dated Mar. 19, 2009, 18 pages.

"Multiple Offerings of Plates, Screws and Pegs", Small Bone Innovations, Inc., 2008, 3 pages.

Stryker, "VariAx Distal Radius: Locking Plate System", www.osteosynthesis.stryker.com, 2006, 12 pages.

\* cited by examiner

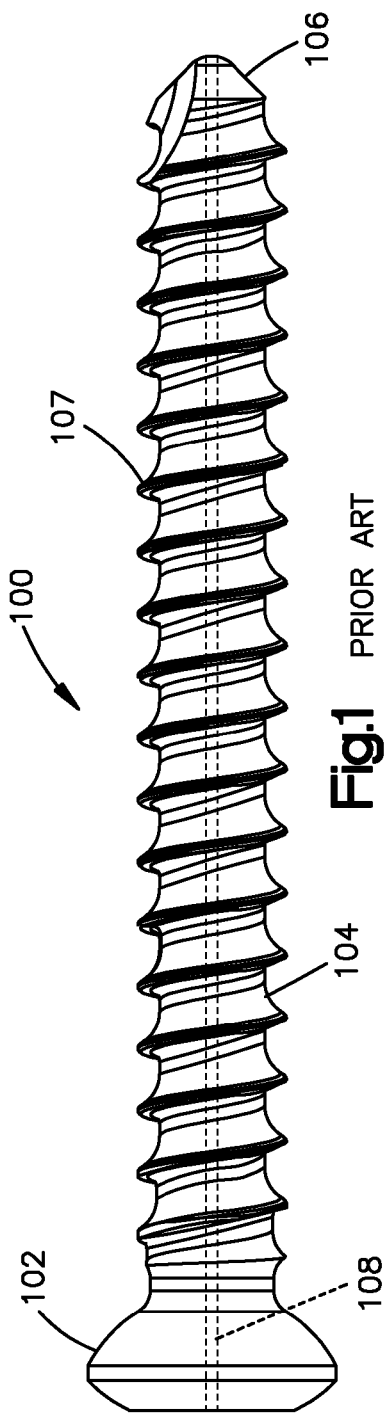
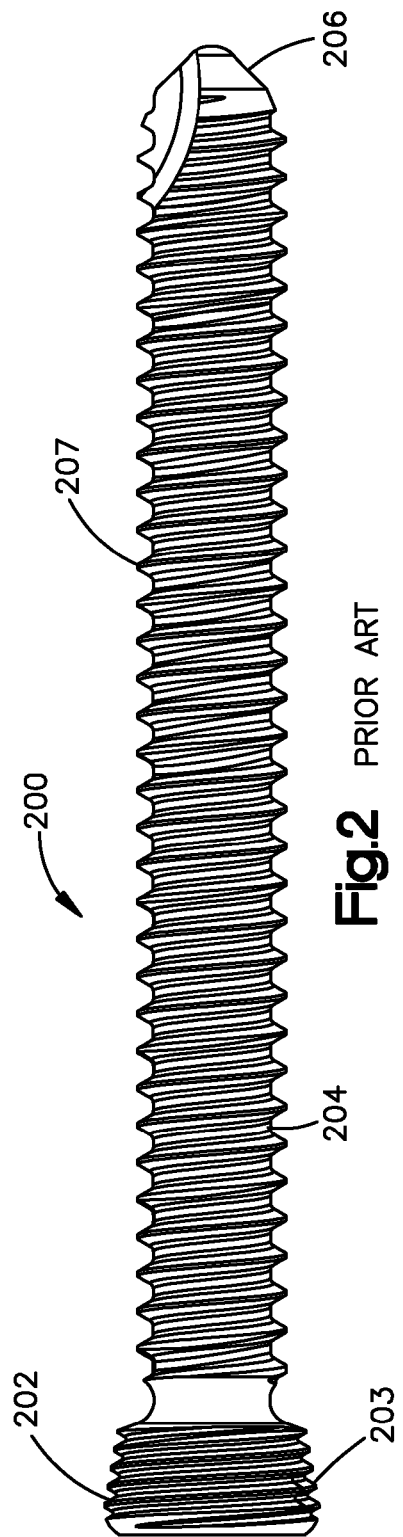

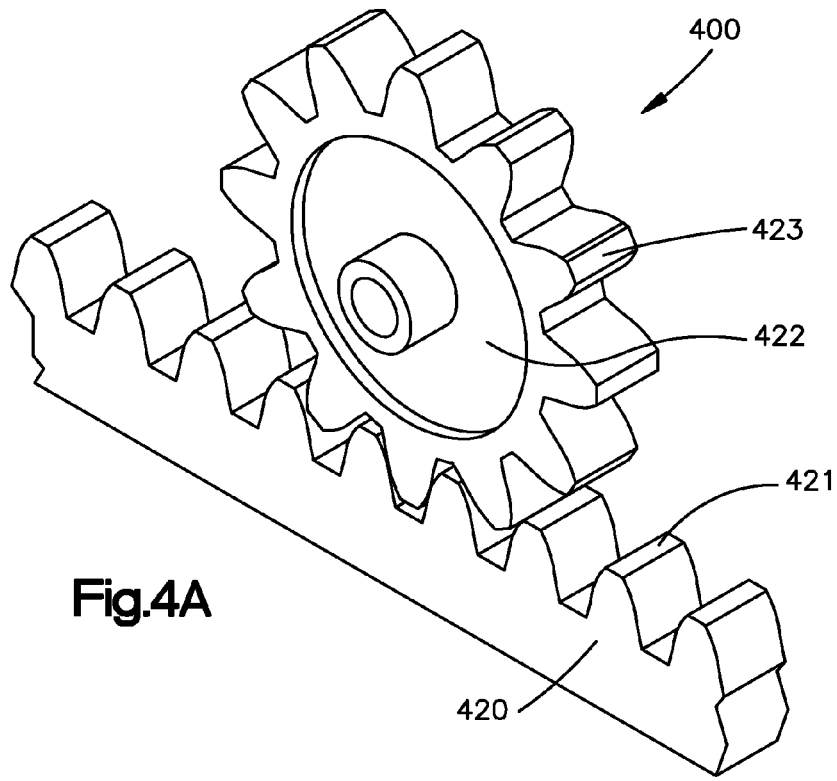
Fig.4A
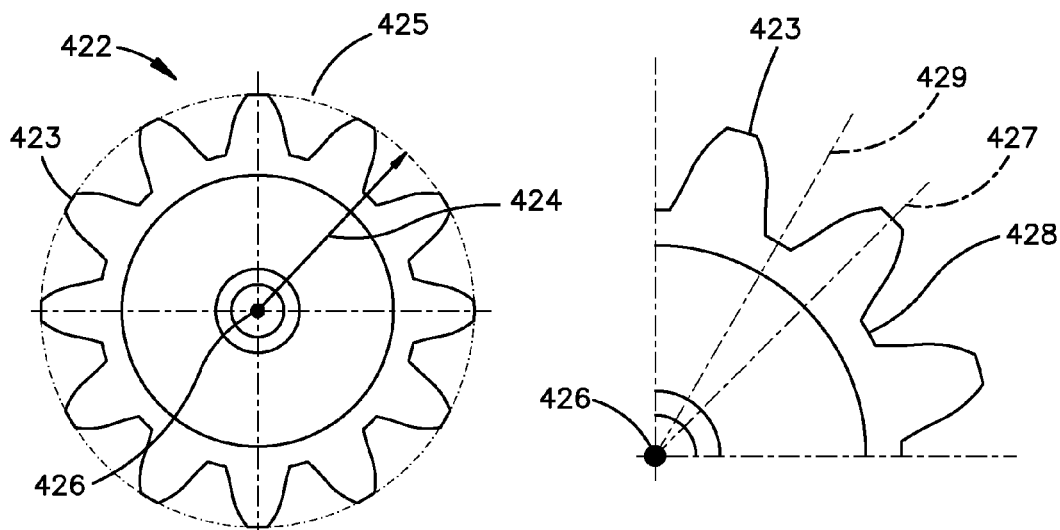
Fig.4B
Fig.4C

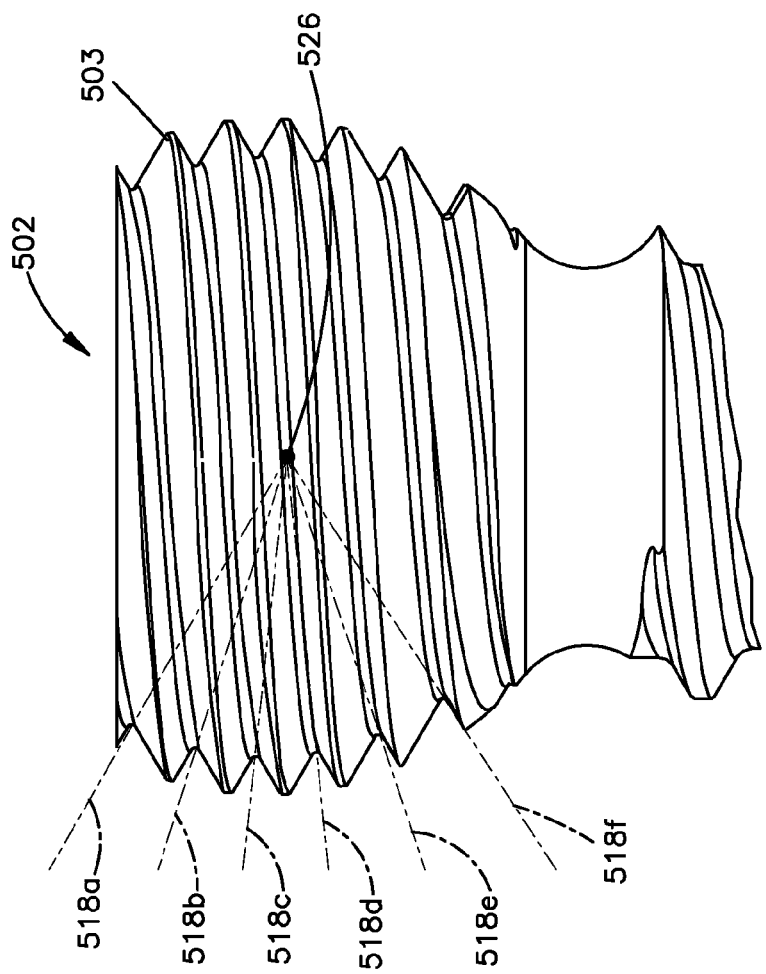
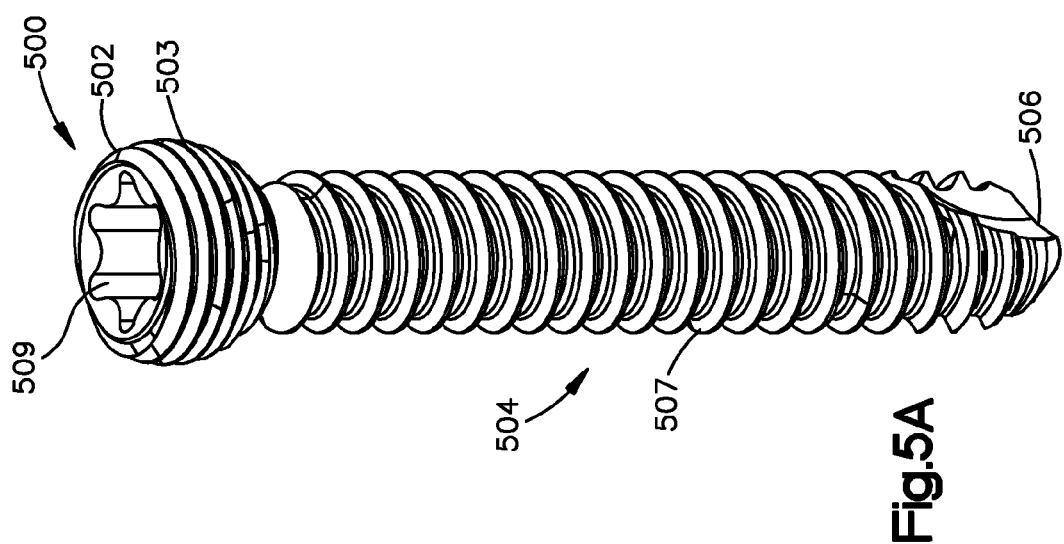

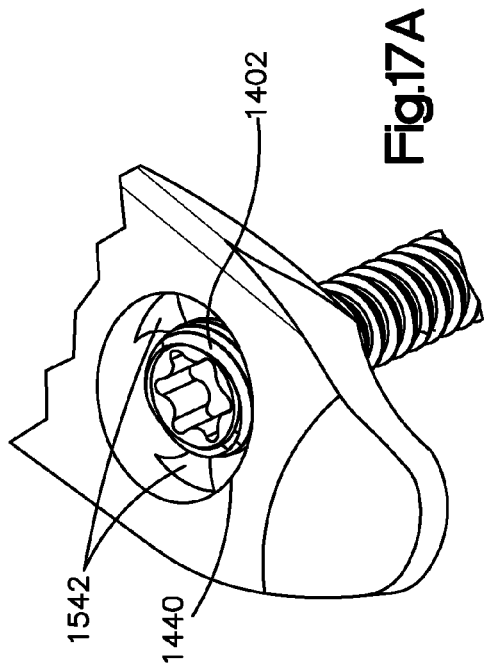
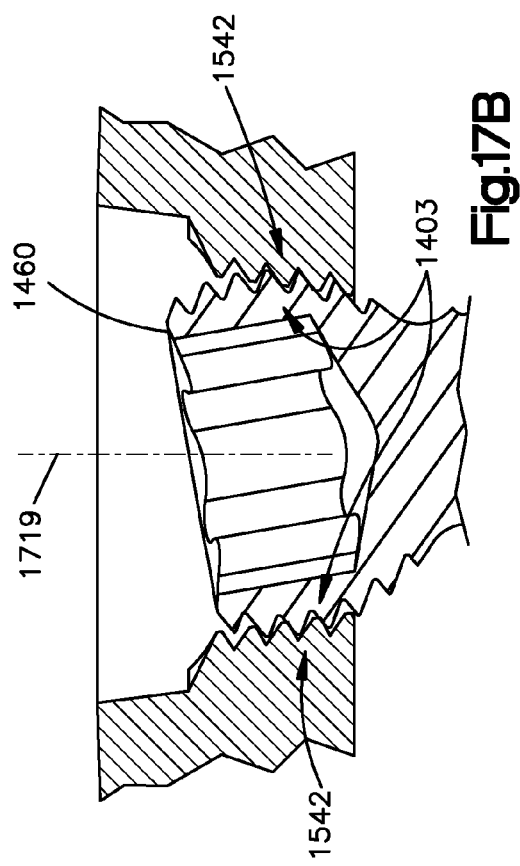

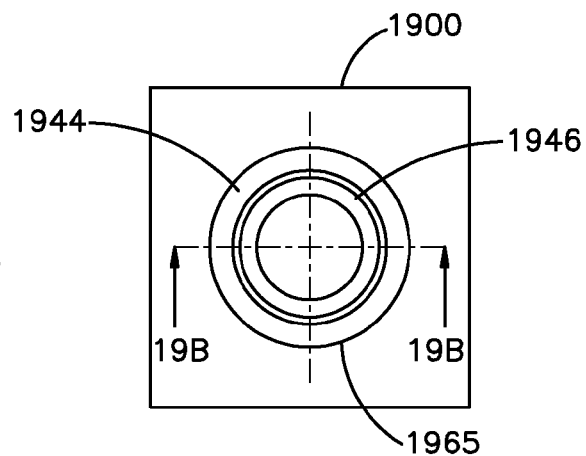
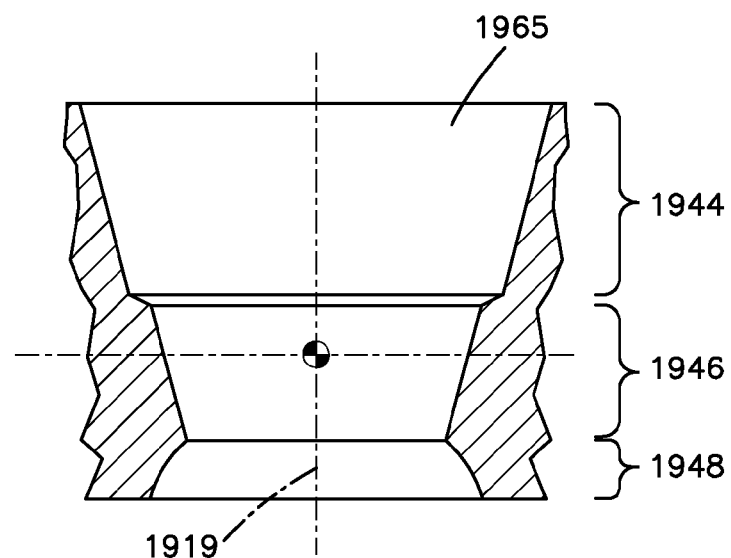
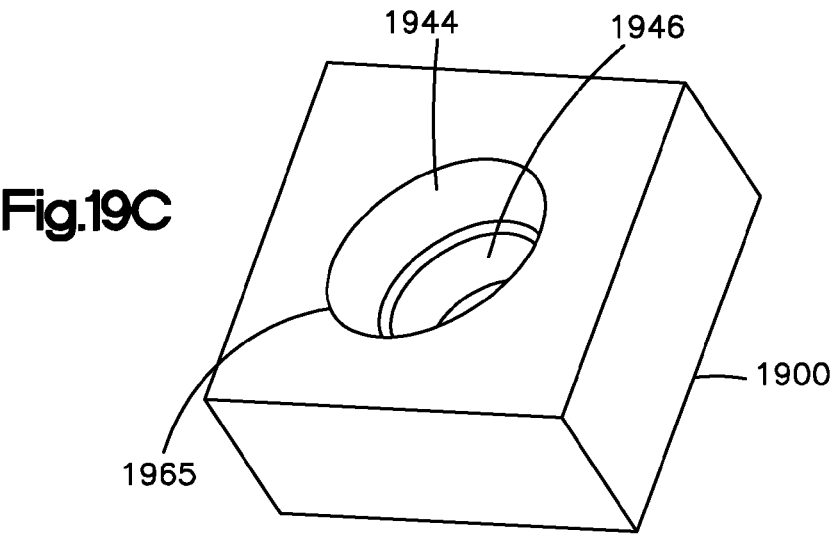

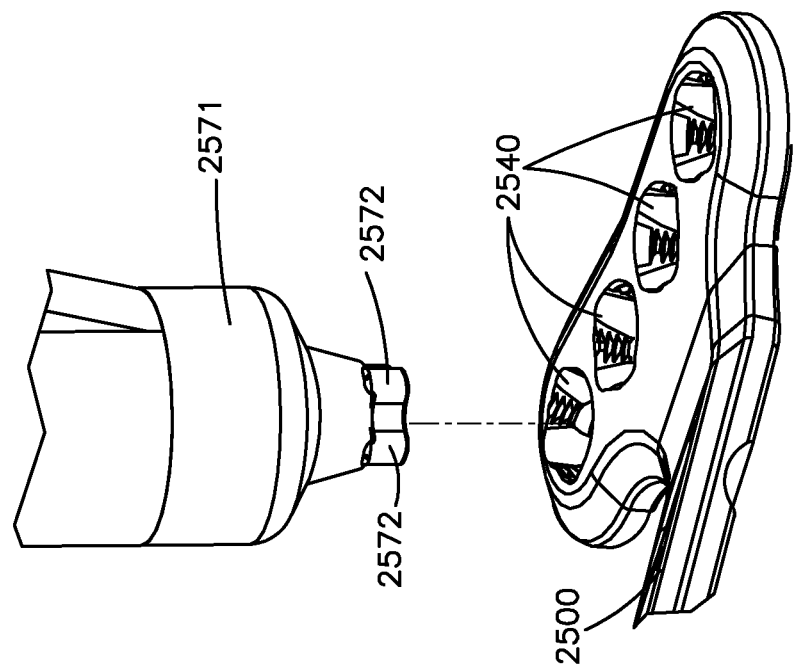
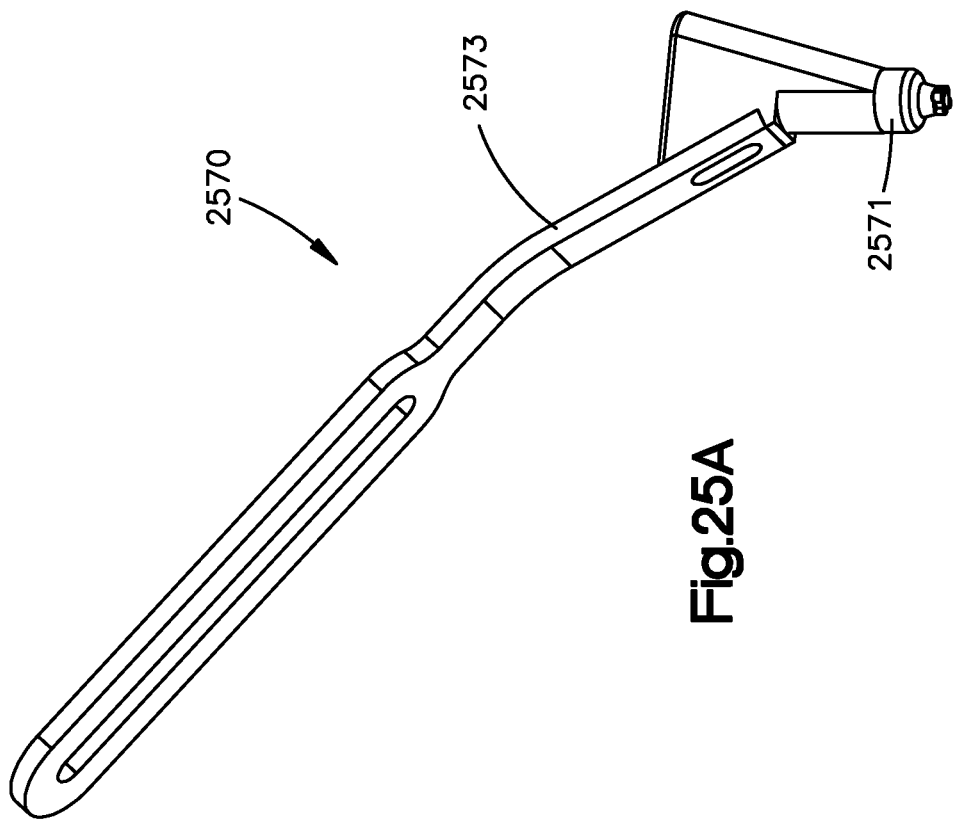
Fig. 25B
Fig. 25A

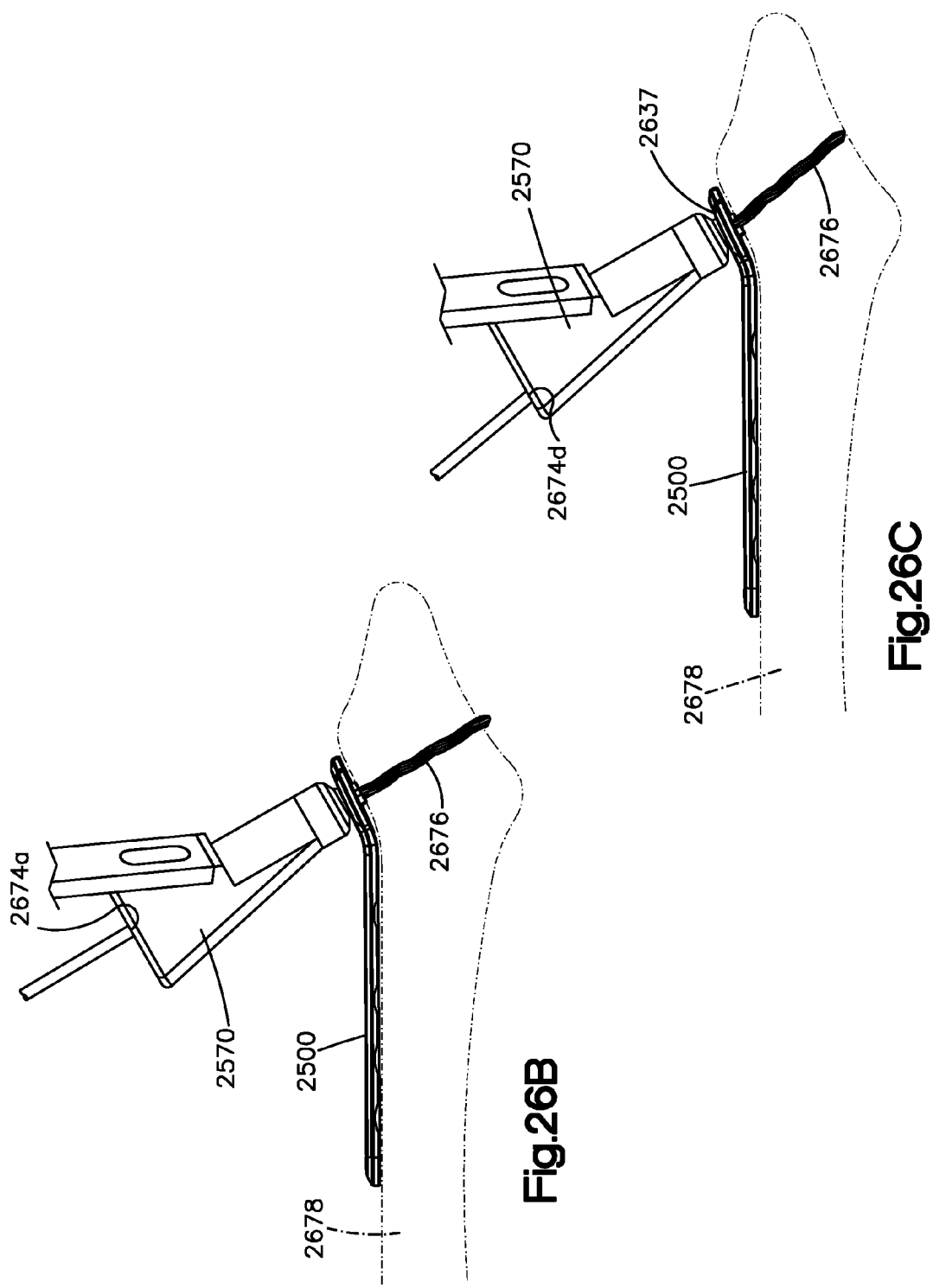

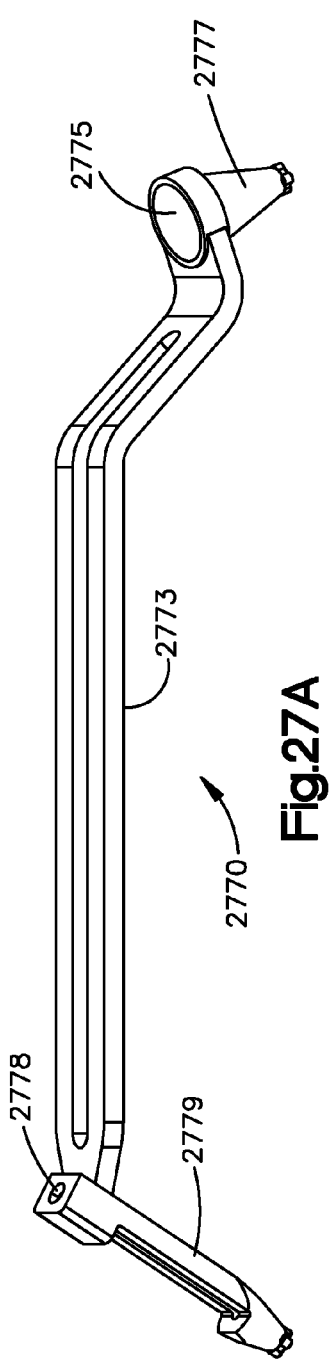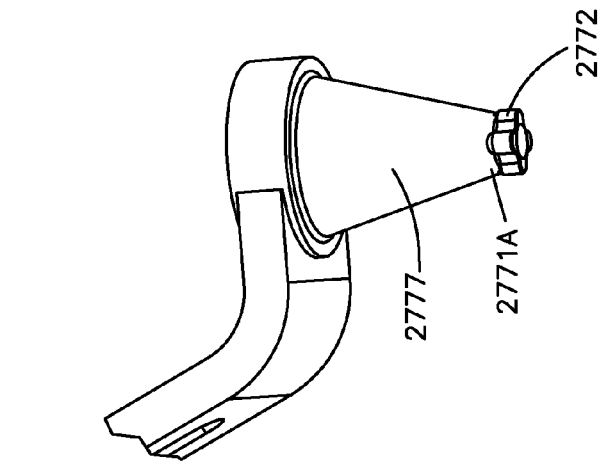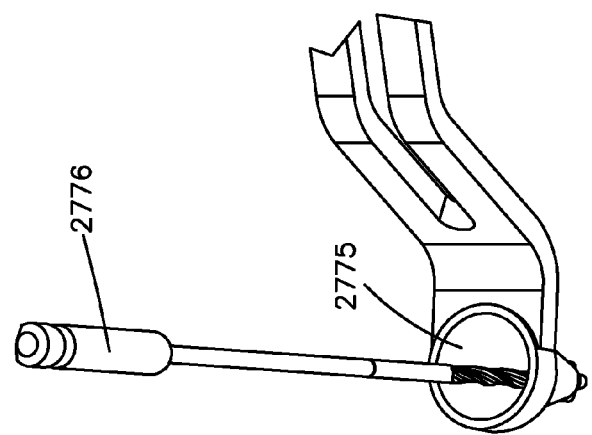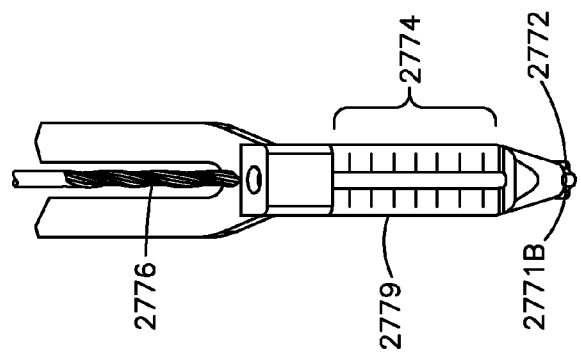

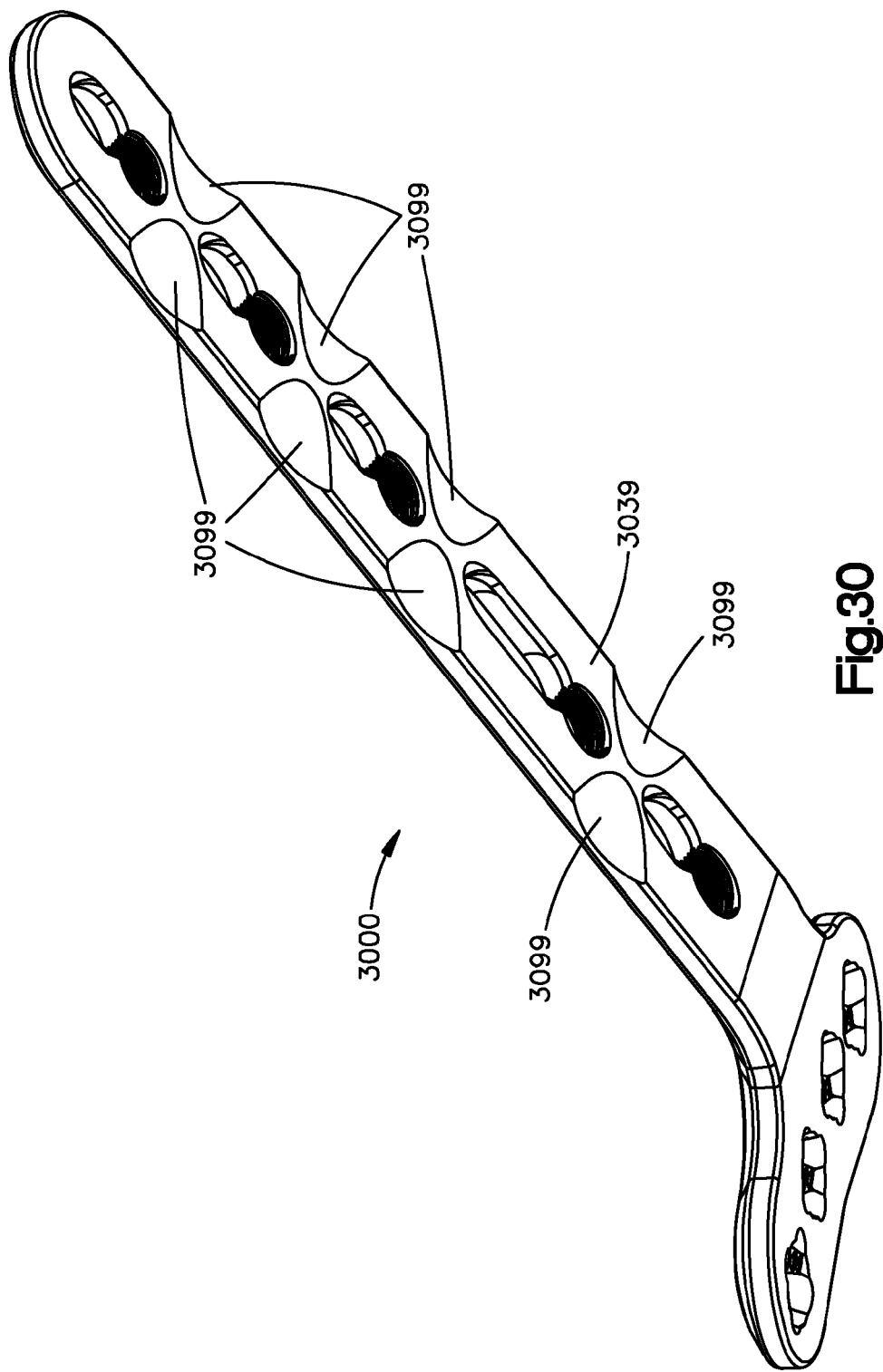

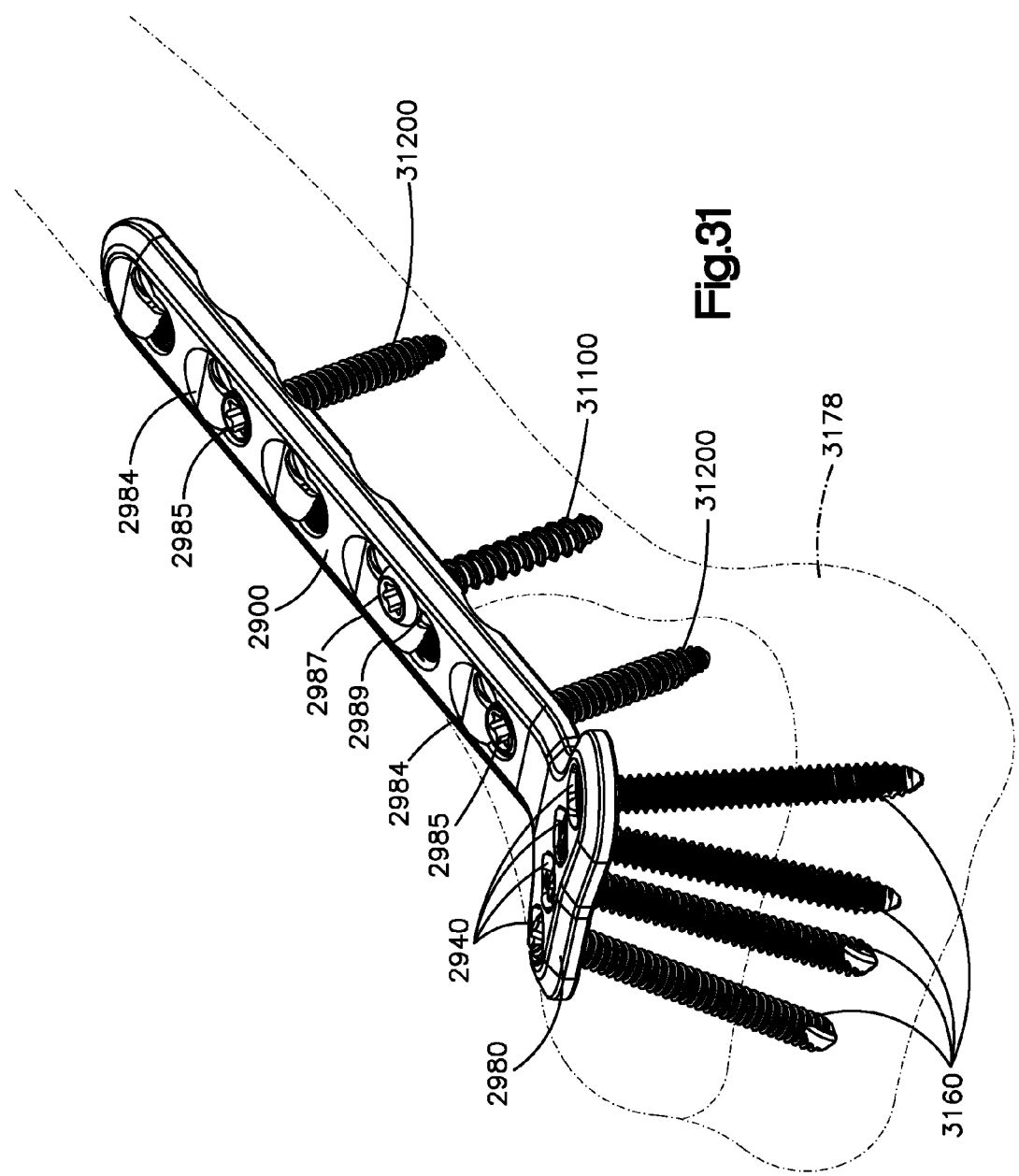

HIGHLY-VERSATILE VARIABLE-ANGLE BONE PLATE SYSTEM

CROSS REFERENCE TO RELATED APPLICATIONS

This application is a continuation of U.S. patent application Ser. No. 11/971,358 filed Jan. 9, 2008. U.S. patent application Ser. No. 11/971,358 filed Jan. 9, 2008 claims the benefit of U.S. Provisional Application No. 60/955,506, filed Aug. 13, 2007 and is a continuation-in-part of U.S. patent application Ser. No. 10/763,689, filed Jan. 26, 2004 which is now U.S. Pat. No. 7,637,928, issue date Dec. 29, 2009, the disclosures of which are hereby incorporated by reference herein in their entireties.

FIELD OF INVENTION

The invention relates to a bone plate system for internal bone fracture fixation. More particularly, the invention relates to a bone plate system that includes bone plates one plate holes constructed to receive non-locking, locking, or variable-angle one screws.

BACKGROUND OF THE INVENTION

Bone plate systems for the internal fixation of bone fractures are well known. Conventional bone plate systems are particularly well-suited to promote the healing of a fracture. A bone screw (also known as a bone anchor) is inserted through a bone plate hole (also known as an anchor hole) and is threaded into bone to compress, neutralize, buttress, tension bend, and/or bridge the fracture ends together and draw the bone against the plate. These screws, which are not secured to the bone plate (and are hereinafter referred to as "non-locking screws"), can be threaded into bone at various angles relative to the bone plate. However, because the screws are not secured to the bone plate, the angular relationships between the plate and screws are not fixed and can change intraoperatively and/or postoperatively. That is, dynamic loading on the bone and bone plate from physiological conditions can cause the screws to loosen or back out with respect to the plate. This can lead to poor alignment and poor clinical results.

Securing the screws to the plate provides a fixed angular relationship between the screws and plate and reduces the incidence of loosening. One known embodiment of screws that can be secured to the bone plate has a screw thread on an outer surface of the screwhead. The thread on the screwhead mates with a corresponding thread on the inner surface of a bone plate hole to lock the screw to the plate. These screws (which are hereinafter referred to as "locking screws") are typically inserted coaxially with the central axis of the hole. Because the relationship between locking screws and the plate is fixed, locking screws provide high resistance to shear, torsional, and bending forces. However, locking screws are limited in their ability to compress bone fragments, which affects healing.

In sum, therefore, an interface formed by a locking screw and bone plate has high resistance to shear forces so as to maintain stability at the screw/plate interface, but has limited ability to compress bone fragments, while an interface formed by a non-locking bone screw and bone plate effectively compresses bone fragments, but has low resistance to shear forces that can lead to screws loosening or backing out. Accordingly, a bone plate system that combines non-locking screws with locking screws is desirable in many clinical situations.

A known bone plate system that can accommodate both locking and non-locking screws includes a bone plate having a plurality of threaded plate holes for receiving locking screws and a plurality of non-threaded plate holes for receiving non-locking screws. However, the non-locking screws in this known system are only used temporarily to keep the plate in place while the locking screws are inserted. The non-locking screws are removed after the locking screws have been inserted. Thus, the long term benefits of combining non-locking screws with locking screws are not obtained.

Another known bone plate system that accommodates both types of screws includes a bone plate with partially threaded plate holes. The partially threaded holes receive either locking or non-locking screws. Because the plate holes are only partially threaded, however, locking screws may not be able to maintain the fixed angular relationship between the screws and plate while under physiological loads. Specifically, the locking screws within the plate are only partially surrounded by threads and thus only partially secured. Under high stress and loading conditions, the locking plate hole may distort and allow the fixed angular relationship between the locking screw and plate to change. This can result in a loss of fixation or plate orientation. Additionally, because of the plate hole geometry, translation of the plate with non-locking screws is limited to one direction only. This may be disadvantageous in bone fracture reduction and manipulation.

Still another known bone plate system that accommodates both types of screws includes a bone plate with threaded and non-threaded plate holes. The threaded plate holes receive locking screws, and the non-threaded plate holes receive non-locking screws, each intended to remain inserted while the plate is implanted. However, because locking screws are effective only when used with threaded holes, a disadvantage of this system is that the number and location of threaded holes in the plate may not be as desired for a particular surgical procedure. For example, there may be one or more non-threaded holes at locations where a surgeon would prefer a threaded hole for insertion of a locking screw.

Further to the known bone plate systems mentioned above it is often desirable for a surgeon to be able to insert a locking bone screw through a bone plate hole at a surgeon-selected angle relative to the bone plate. A number of so-called "polyaxial" bone plate systems are known. Many use a bushing located in a plate hole to lock the degree of screw angulation relative to the plate. In one such system, the bushing is rotatable within the plate hole. A so-called "variable-angle locking" screw is threaded into bone through the bushing and plate hole. As the screw is threaded into bone, the threaded tapered head of the screw engages a threaded internal surface of the bushing to expand the bushing against the inner surface or wall of the plate hole, thereby friction locking the screw at the desired angle relative to the bone plate.

In another known polyaxial bone plate system, a bushing is seated at a desired angle in a plate hole. A fastening screw having an expandable head with a threaded recess is inserted through the bushing and threaded into bone. A locking screw is then threaded into the recess of the screwhead to expand the head outward against the bushing to lock the selected angle of the screw relative to the bone plate.

In still another known polyaxial bone plate system, an expandable ring is positioned in the plate hole. As a bone screw with a tapered head engages the ring and is threaded into bone, the ring expands against the inner surface or wall of the hole to lock the selected angle of the screw relative to the bone plate.

However, these polyaxial bone plate systems have multiple components that can be cumbersome and tedious to manipulate during surgery and more particularly, for example, it is possible that the bushing or expandable ring may pop out during surgery.

In view of the foregoing, it would be desirable to be able to provide an improved bone plate system that overcomes the deficiencies and disadvantages of known bone plate systems.

SUMMARY OF THE INVENTION

The invention provides a highly-versatile variable-angle bone plate system for fixing bone fractures. The system includes bone plates having a plurality of bone plate holes that pass completely through the bone plate, from a top surface of the plate to a bottom bone-contacting surface of the plate. The holes are constructed advantageously to receive either a non-locking, locking, or variable-angle locking bone screw. Instead of screw threads as is known in conventional bone plate holes, the inner surface of the plate holes has discrete columns of protrusions selected from the group containing teeth, thread segments, pegs and spikes for engaging compatibly dimensioned and configured threaded heads of locking and variable-angle locking bone screws.

The invention advantageously permits conventional non-locking bone screws of compatible size and screwhead shape to be used in the bone plate holes. Non-locking bone screws have a threaded shaft for engaging bone and a screwhead having no means or structures (e.g. threads) thereon for securing or locking to the bone plate. A non-locking screw may be received in the bone plate hole at any desired angle, whereupon the shaft of the screw is driven into the bone until the head of the screw is seated as desired in the bone plate hole.

The invention also advantageously permits conventional locking bone screws of compatible size, screwhead shape, and screwhead thread to be used in the bone plate holes. These locking bone screws have a threaded shaft for engaging bone and a screw thread on an outer surface of the screwhead that can advantageously engage the columns of thread segments in the bone plate hole. Locking bone screws are received in the bone plate holes coaxial to the central axis of the hole. That is, for example, if the central axis of the hole is perpendicular to the top surface of the bone plate, a locking bone screw is received in a bone plate hole of the invention at about a 90 degree angle with respect to the top surface. The shaft of the locking screw is driven into bone until the screwhead engages the bone plate hole, whereupon the screwhead threads engage the columns of thread segments in the bone plate hole. The screw is then driven until the screwhead is threaded as desired into the bone plate hole, which fixes the screw to the plate.

A variable-angle locking bone screw according to the invention is inserted through a bone plate hole and locked to the bone plate at a selectable angle within a range of selectable angles. The range of selectable angles in one embodiment forms a cone of about 30 degrees about the central axis of the hole. In other words, the angle of the screw can vary from 0 degrees to about 15 degrees in any direction away from the central axis of the hole. Variable-angle locking screws of the invention advantageously do not require a bushing, a compression cap, an expandable ring, or an expandable head to lock the angular position of the screw relative to the bone plate.

Variable-angle locking screws of the invention advantageously have a head that is at least partially spherically-shaped. The spherically-shaped portion of the head has an external screw thread on its outer surface. The profile of the screw thread follows the arc-shaped (i.e., non-linear) outer radius of curvature of the spherically-shaped portion. Each thread peak and each thread trough (or crest and root in thread terminology, respectively) lies on a respective radius of curvature coinciding with or parallel to/concentric with (i.e., having the same center as) the radius of curvature of the spherically-shaped portion of the screwhead. In other words, the peaks may lie on a "major" radius of curvature, which coincides with the radius of curvature of the spherically-shaped portion, while the troughs lie on a "minor" radius of curvature, wherein the major and minor radiuses of curvature have the same center, thus forming concentric circles. Note that this radius of curvature center is not necessarily the center of the screwhead. In one embodiment, the thread profile has profile lines that intersect the center of the radius of curvature of the screwhead. Profile lines represent an extension of the longitudinal axis of a cutting bit of a thread cutter as the cutting bit contacts a surface in which a thread is cut. Conventional locking screwheads, in contrast, have thread peaks and troughs (viewed in profile) that lie on respective substantially straight, parallel lines, and the profile lines of those peaks and troughs extend parallel to each other and do not intersect the center of the radius of curvature of the screwhead (except perhaps the profile line of one peak or trough that happens to be aligned with the center).

To facilitate threading into bone, each of the bone screws may be self-tapping and/or self-drilling. Each of the bone screws also may be cannular for insertion of a guide wire to guide screw placement.

Bone plates of the invention are not limited to any particular shape, size, or configuration. For example, in one embodiment, the bone plate has a head portion and a shaft portion. The head portion is configured and dimensioned to conform to a metaphysis of a bone, and the shaft portion is configured and dimensioned to conform to a diaphysis of a bone. In another example embodiment, the head portion has a curved surface and includes an anterior fork substantially parallel to an anterior side of the shaft portion and a posterior fork extending out from a posterior side of the shaft portion. In still another example embodiment, the head portion flares outward from the shaft portion and is curved, tapered, and twisted.

Bone plate holes of the invention are not limited to any particular number or arrangement. Optionally, bone plate holes of the invention may have elongated non-threaded portions to increase the versatility of placing non-locking screws. Bone plates of the invention may also optionally have suture holes and conventional threaded and/or non-threaded screw holes, although neither type of conventional hole is necessary nor recommended.

The invention also provides a method of bone fracture fixation. The method includes positioning a bone plate against bone, selecting a bone plate hole for inserting there through a bone screw, selecting a non-locking, locking, or variable-angle locking bone screw, inserting the selected bone screw through the selected bone plate hole and, if applicable, selecting an insertion angle with respect to the central axis of the hole, and driving the screw into the bone until the screwhead is seated in or secured to the bone plate hole to either compress the bone plate against the bone or fix the relationship between the screw and the bone plate. The bone screws remain in the bone for substantially as long as the bone plate is implanted.

BRIEF DESCRIPTION OF THE DRAWINGS

The above and other advantages of the invention will be apparent upon consideration of the following detailed description, taken in conjunction with the accompanying drawings, in which like reference characters refer to like parts throughout, and in which:

FIG. 1 is an elevational view of a conventional non-locking bone screw;

FIG. 2 is an elevational view of a conventional locking bone screw;

FIG. 4A is a perspective view of a rack and pinion gear;

FIG. 4B is an elevational front view of the pinion gear of FIG. 4A;

FIG. 4C is an enlarged sectional view of the pinion gear of FIG. 4B;

FIG. 5A is a perspective view of a variable-angle locking screw according to the invention;

FIGS. 5B and 5C are front elevational and cross-sectional views, respectively, of the head of the variable-angle locking screw of FIG. 5A;

FIGS. 17A and 17B are perspective and elevational front views, respectively, of a variable-angle locking screw driven into a bone plate hole according to the invention;

FIGS. 25A-C, 26A-C, and 27A-D are various perspective views of drill guides used with a bone plate according to the invention;

FIG. 30 is a perspective view of the underside of a bone plate according to the invention;

FIG. 31 is a perspective view of a bone plate applied to a bone fracture according to the invention;

DETAILED DESCRIPTION OF THE INVENTION

Figure 3A:
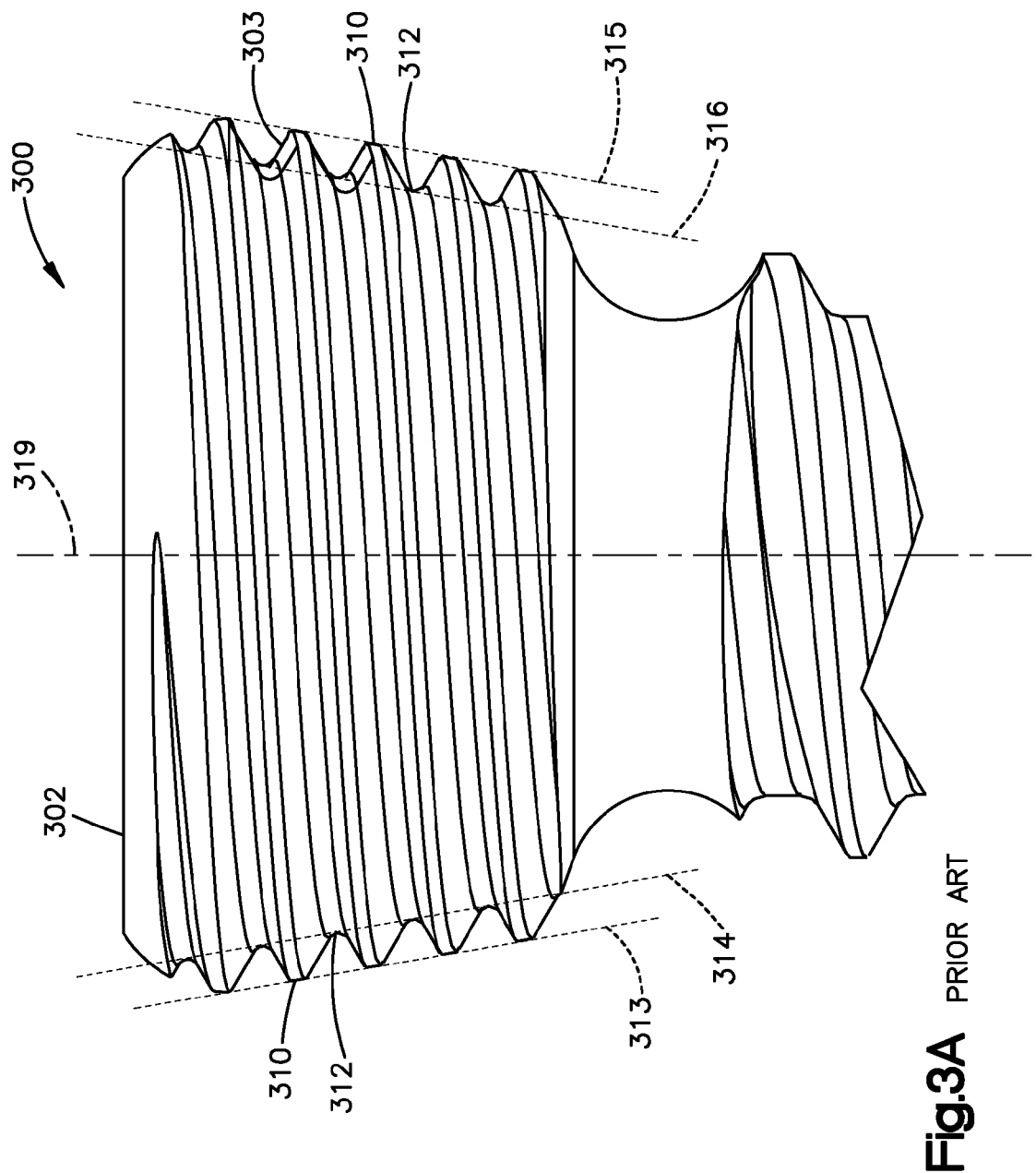
FIGS. 3A and 3B are elevational and cross-sectional views of the head of a conventional locking bone screw.

A bone plate system according to the invention includes a bone plate, variable-angle locking screws, non-locking screws, and optionally locking screws. The bone plate advantageously has bone plate holes having discrete columns of protrusions around an inner surface of the hole. The bone plate may also have combination bone plate holes that have a portion with columns of thread segments and a portion without thread segments or threads. Both types of bone plate holes advantageously are constructed to receive non-locking, locking, and variable-angle locking screws. Optionally, bone plates of the invention may additionally have suture holes, and while unnecessary, conventional threaded holes, smooth holes (i.e., holes without thread segments or threads) and/or combination holes thereof.

FIG. 1 shows a typical non-locking bone screw 100, also known as a cortex screw. Generally, any surgical bone screw having a non-threaded head 102 with a generally smooth surface and of an appropriate size and geometry for a selected plate hole can be used with the invention. The shape of head 102 may be, for example, conically tapered, straight-sided, spherical, hemispherical, etc. Non-locking screw 100 has a shaft 104 that is at least partially threaded for attachment to bone. The length of shaft 104 and the thread configuration (e.g., pitch, profile, etc.) of shaft thread 107 can vary depending on the application. As is known in the art, tip 106 and shaft threads 107 may be self-tapping and/or self-drilling to facilitate implantation into bone. Head 102 and shaft 104 may also have a cannula 108 for receiving a guide wire to aid in proper placement.

FIG. 2 shows a typical locking screw 200. Generally, any surgical bone screw having a threaded head 202 can be used with the invention provided that head 202 is of an appropriate size and geometry for a selected plate hole and that threads 203 mate with the columns of thread segments in the plate hole. The shape of head 202 is typically conically tapered, but also may be, for example, straight-sided. Locking screw 200 has a shaft 204 that is at least partially threaded for attachment to bone. The length of shaft 204 and the thread configuration (e.g. pitch, profile, etc.) of shaft thread 207 can vary depending on the application. As is known in the art, tip 206 and shaft threads 207 may be self-tapping and/or self-drilling to facilitate implantation into bone. Head 202 and shaft 204 may also be cannular for receiving a guide wire to aid in proper placement.

Figures 3B, 3C:
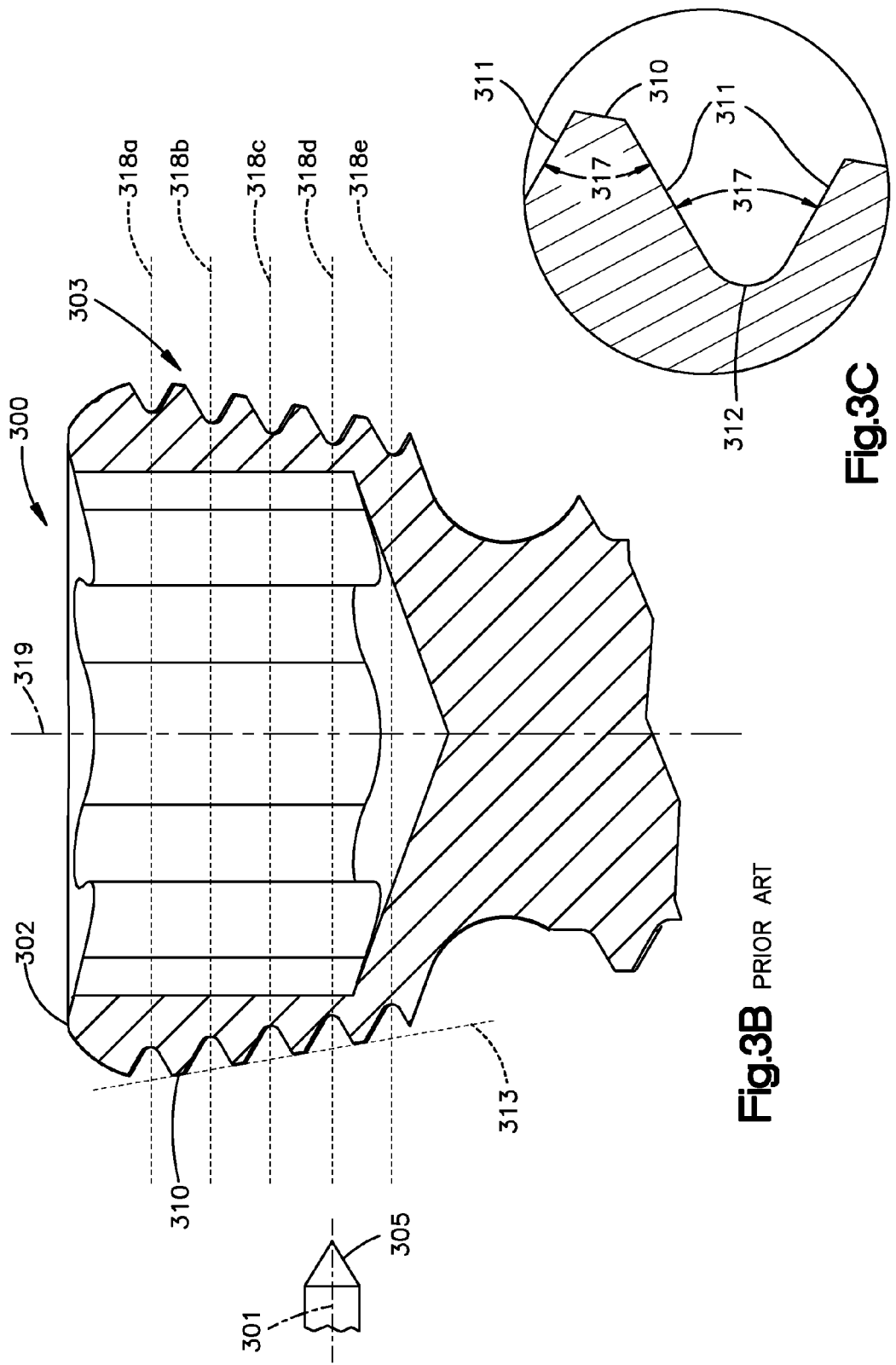
FIG. 3C is an enlarged, partial cross-sectional view of the locking bone screw of FIGS. 3A and 3B.

FIGS. 3A and 3B show head 302 of a typical locking screw 300. The profile of thread 303 on head 302 includes thread peaks 310 and troughs 312 connected to each other by flanks 311, two adjoining flanks 311 forming a thread angle 317, as shown in FIG. 3C. Head 302, which is conically shaped as is usual on known locking screws, is typically oriented such that thread peaks 310 lie on a straight line, such as lines 313 or 315, and thread troughs 312 lie on another straight line, such as lines 314 or 316, wherein the pairs of lines (313, 314) and (315, 316) are parallel to each other. Furthermore, the thread profile lines of each thread peak 310 and each thread trough 312 extend parallel to each other and perpendicular or normal to the central axis 319 of the screw, as represented by trough profile lines 318a-e shown in FIG. 3B. Profile lines 318a-e are formed by extending the longitudinal axis 301 of a cutting bit 305 of a thread cutter as the cutting bit contacts the outer surface of head 302 to cut thread 303. A typical locking screw also has a constant thread pitch (the distance from peak to peak, trough to trough, or profile line to profile line) as measured along the central axis (e.g., 319).

A variable-angle locking screw according to the invention has a screwhead that is at least partially spherical. The spherically-shaped portion of the head has a thread on an outer surface thereof which is preferably a double lead thread. The thread has a profile that follows the arc-shaped (i.e., non-linear) radius of curvature of the spherically-shaped portion of the head. Note that the thread pitch is constant as measured along the radius of curvature, but varies from narrow-to-wide-to-narrow as measured along the central axis of the screw from one end (e.g. the top) of the spherically-shaped portion of the head to the other end (e.g. the bottom) (see, e.g. FIGS. 32-35 and the description thereof further below). This thread profile allows the variable-angle locking screw to engage a bone plate hole of the invention at a selectable angle within a range of angles while advantageously maintaining the same degree of contact with the bone plate regardless of the angle chosen. That is, the angle of the screw with respect to the central axis of the bone plate hole within the permissible range of angles does not affect the engagement of the screwhead thread with respect to the inner surface of the plate hole. A tight lock is advantageously obtained between the screw and the bone plate regardless of the angle (within the range of angles) at which the screw is inserted into the bone plate hole, because the threads on the spherically-shaped portion of the screwhead engage the columns of thread segments in precisely the same manner, ensuring a good fit.

Some of the advantageous features of the bone plate system of the invention may be explained with the aid of an analogy with rack and pinion gears. Although bone plate systems and rack and pinion gears are very much unrelated (rack and pinion gears are used, for example, in automotive steering mechanisms and locomotive and railcar drive mechanisms), the bone plate system of the invention shares an analogous concept. As shown in FIGS. 4A-C, rack and pinion gear 400 has a rack 420 having teeth 421 and a circular pinion 422 having teeth 423. Rotational motion applied to pinion 422 causes rack 420 to translate while, conversely, linear motion or translation of rack 420 causes pinion 422 to rotate.

The analogous concept is the arrangement of teeth 423 around the radius of curvature 425 of pinion 422. Gear teeth 423, shown in profile in FIGS. 4B and 4C, are equally angularly spaced and follow radius of curvature 425. Moreover, each tooth 423 is oriented such that a line bisecting the tooth 423, as represented by line 427, intersects the center 426 of the radius of curvature 425, which forms a circle having a radius 424. Similarly a line bisecting any space 428 between adjacent teeth 423, as represented by line 429, also intersects center 426. The thread profile of the head of a variable-angle locking screw (viewed in a direction perpendicular to the central axis of the screw) according to the invention is analogous to that of the sectional profile view of the pinion teeth 423 and spaces 428 of FIG. 4C.

Figure 5C:
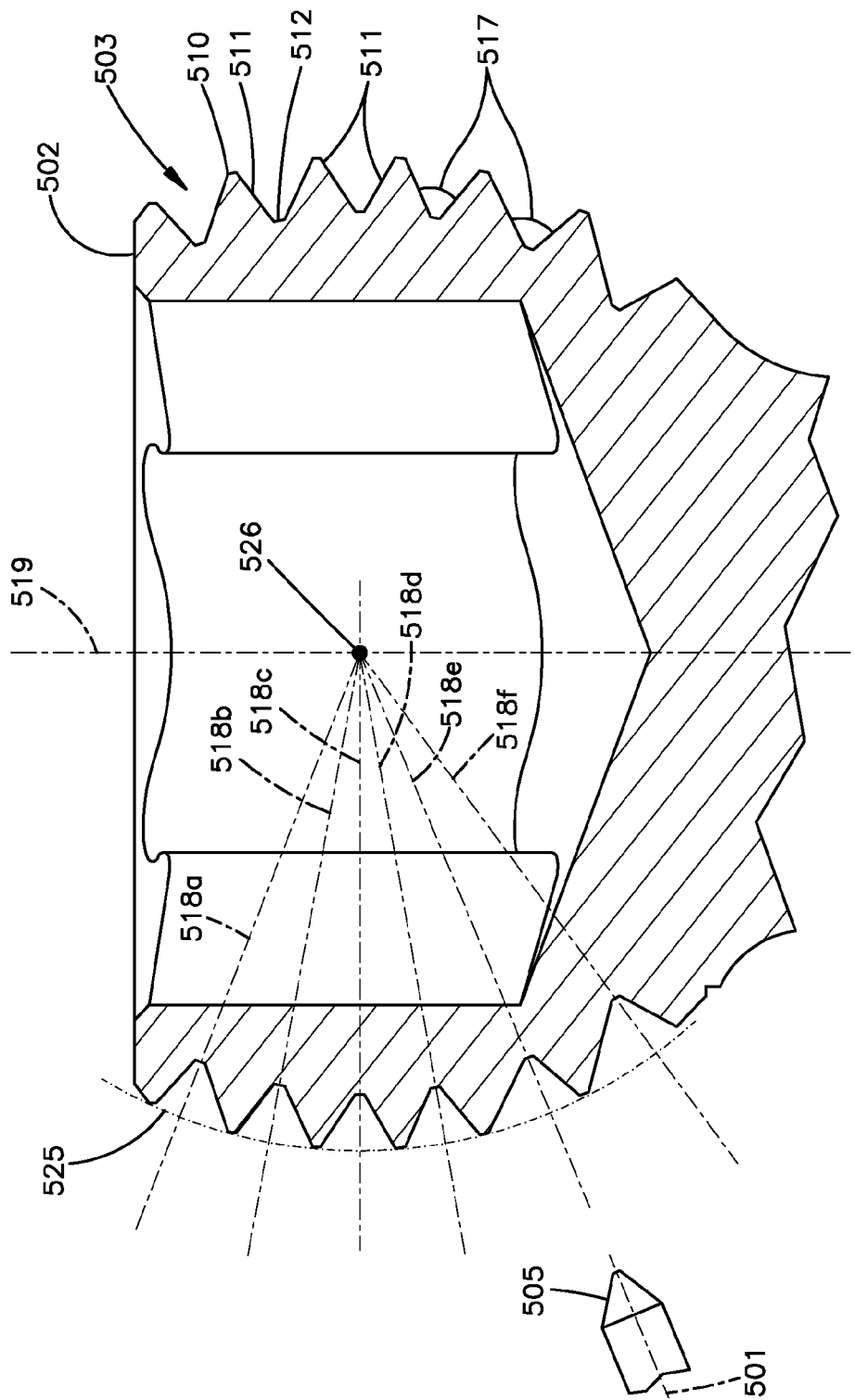

FIGS. 5A-C show an embodiment of a variable-angle locking screw according to the invention. Variable-angle locking screw 500 has a partially-spherical head 502 and a shaft 504. Head 502 has a thread 503, and shaft 504 has a thread 507. Head 502 preferably has a recess 509 for receiving a tool to drive and extract the screw into and out of bone and into and out of a bone plate hole. Preferably, tip 506 and shaft thread 507 are self-tapping and/or self-drilling to facilitate implantation into bone. Head 502 and shaft 504 may be cannular for receiving a guide wire to aid in proper placement. FIGS. 5B and 5C show the profile of thread 503, which advantageously follows the radius of curvature 525. In one embodiment, the radius is about 2 mm. Respective peaks 510 and troughs 512 of thread 503 as seen in profile are preferably separated by equal angular increments. Peaks 510 and troughs 512 are connected by flanks 511 at thread angles 517, which in this embodiment, are preferably about 60 degrees. The thread profile lines 518a-f extend through troughs 512 and result in a series of lines that intersect the center 526 of the radius of curvature 525. Profile lines 518a-f are formed by extending the longitudinal axis 501 of a cutting bit 505 of a thread cutter as the cutting bit contacts the outer spherical surface of head 502 to cut thread 503. In this embodiment, cutting bit 505 is always normal to the outer spherical surface of head 502 as thread 503 is cut. Also in this embodiment, the radius of curvature is such that the radius center 526 lies on the central axis 519 of screw 500. Depending on the length of the radius and the dimensions of the screw, center 526 may or may not lie on the central axis of the screw. Moreover, as the radius increases while the dimensions of the screw remain constant, the radius center will move outside the screwhead, as shown, for example, in FIG. 6.

Figure 6:
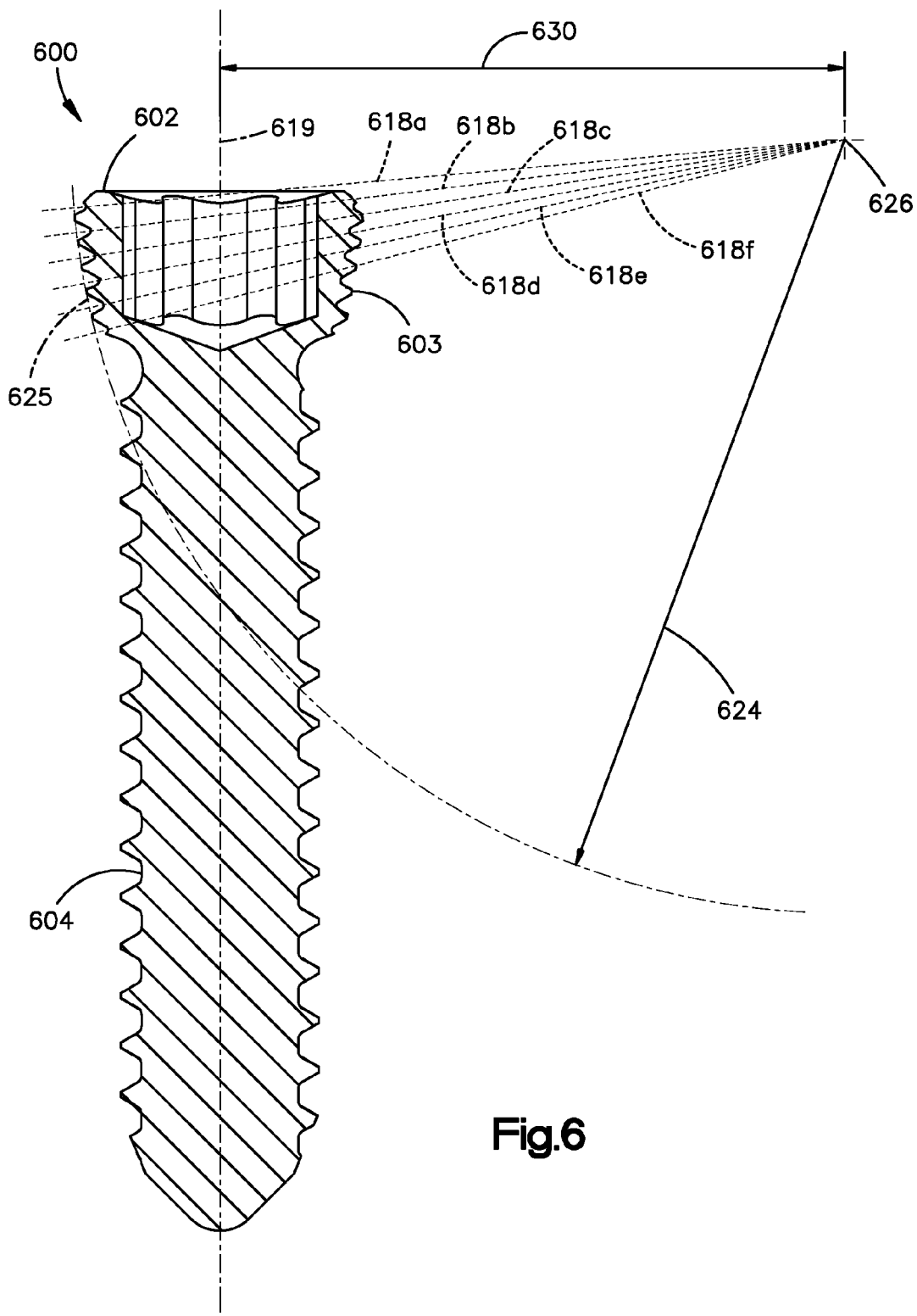
FIG. 6 is a cross-sectional view of another embodiment of a variable-angle locking screw according to the invention.

FIG. 6 shows another embodiment of a variable-angle locking screw of invention. In this embodiment, screwhead 602 of variable-angle locking screw 600 has a larger radius of curvature 625 than screw 500. This results in trough profile lines 618a-f intersecting radius of curvature center 626, which is a distance 630 (measured perpendicularly) from central axis 619 of screw 600. If, for example, radius 624 is 10 mm, distance 630 may be about 8.2 mm for a 2.4 mm screw (the 2.4 mm refers to the major diameter of shaft 604). Note, however, that as the radius of curvature increases, the screwhead becomes less and less spherical in shape, causing the thread profile to become more and more aligned with a straight line (such as, e.g., lines 313-316) as in known locking screwheads.

Figure 7:
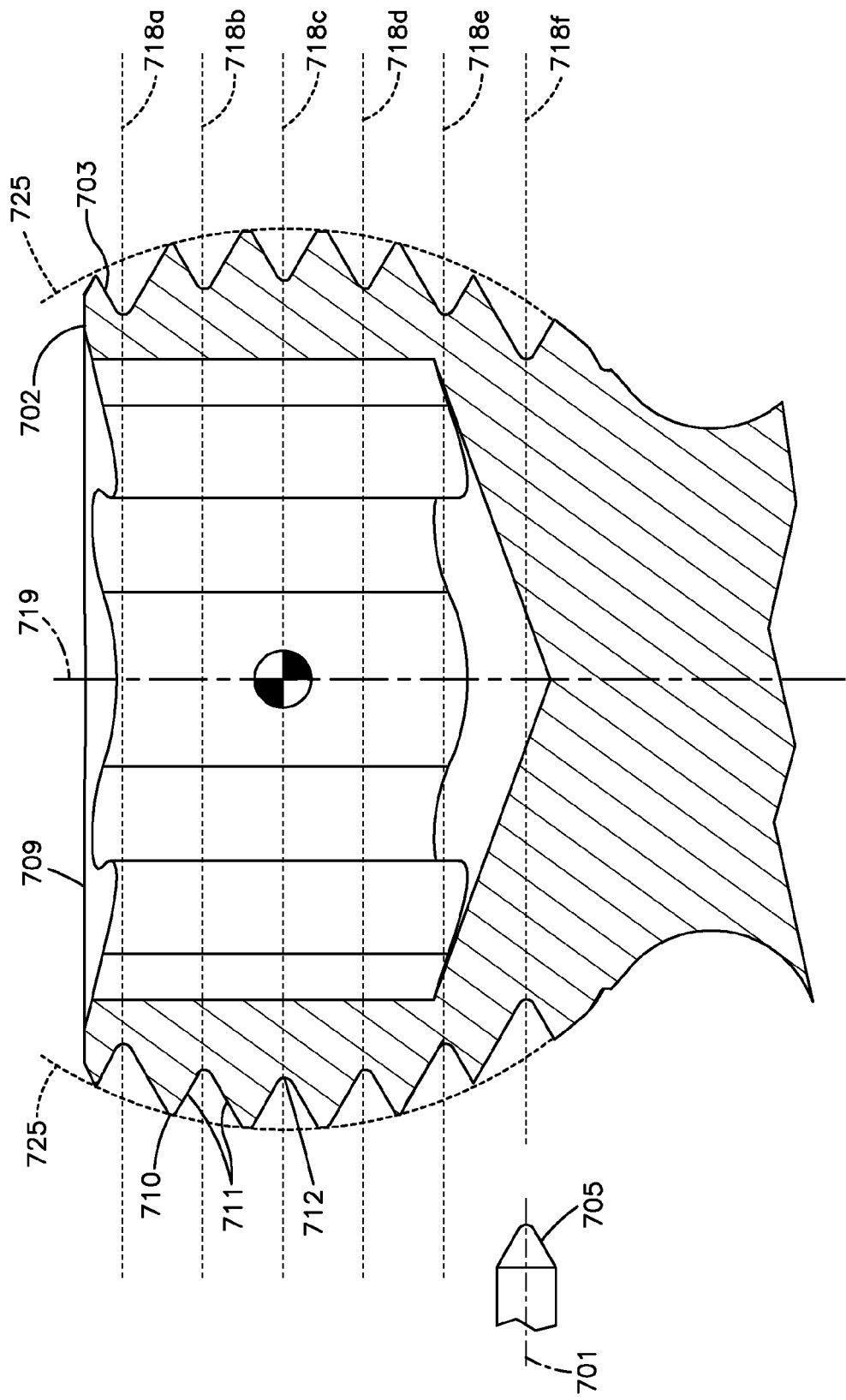
FIG. 7 is a cross-sectional view of a still another embodiment of a variable-angle locking screwhead according to the invention.

FIG. 7 shows still another embodiment of a variable-angle locking screwhead in accordance with the invention. Screwhead 702 has a central axis 719, thread 703, and a recess 709 for receiving a driving/extracting tool. As in previous embodiments, the profile of thread 703 advantageously follows the arc-shaped (i.e., non-linear) radius of curvature 725 and includes thread peaks 710, troughs 712, and flanks 711. However, unlike previous embodiments, the thread profile lines do not intersect the center of the radius of curvature. Instead, the thread profile lines, represented by trough profile lines 718a-f, extend parallel to each other and perpendicular to central axis 719. These lines extend in this manner because of the way in which cutting bit 705 of a thread cutter contacts the outer spherical surface of head 702 to cut thread 703, lines 718a-f representing extensions of longitudinal axis 701 of cutting bit 705. Functionally, this difference results in a less ideal screwhead/hole thread engagement. However, screwhead 702 is currently easier to fabricate than screwhead 502.

Figure 8:
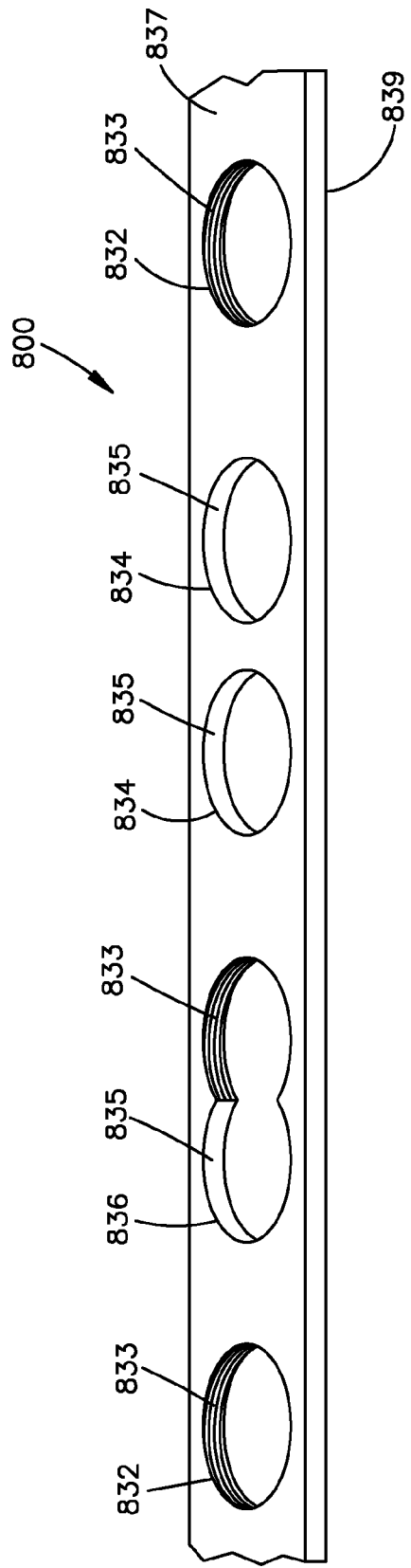
FIG. 8 is a perspective view of a portion of a bone plate with conventional locking, non-locking, and combination locking/non-locking bone plate holes.

FIG. 8 shows a bone plate 800 having conventional bone plate holes including locking bone plate holes 832, non-locking bone plate holes 834, and a combination locking/non-locking bone plate hole 836. Each type of hole extends from the top surface 837 completely through to the bottom bone-engaging surface 839. Locking plate holes 832 have threads 833 extending around the inner surface of the hole for engaging the threads around the head of a locking bone screw. Conventional locking plate holes may have threads 833 extending completely through from top surface 837 to bottom surface 839, as shown, or may alternatively have threads extending for only a portion of the vertical distance between the top and bottom surfaces of the bone plate. Non-locking plate holes 834 have non-threaded or smooth inner surfaces 835 for accommodating the head of a non-locking bone screw. Combination locking/non-locking plate hole 836 increases the versatility of the bone plate by allowing the surgeon to use either a locking screw or a non-locking screw through the hole. Combination hole 836 has one end with threads 833 around the inner surface of the hole for receiving a locking bone screw and the other end with a smooth or non-threaded inner surface 835 for alternatively receiving a non-locking bone screw.

Figure 9B:
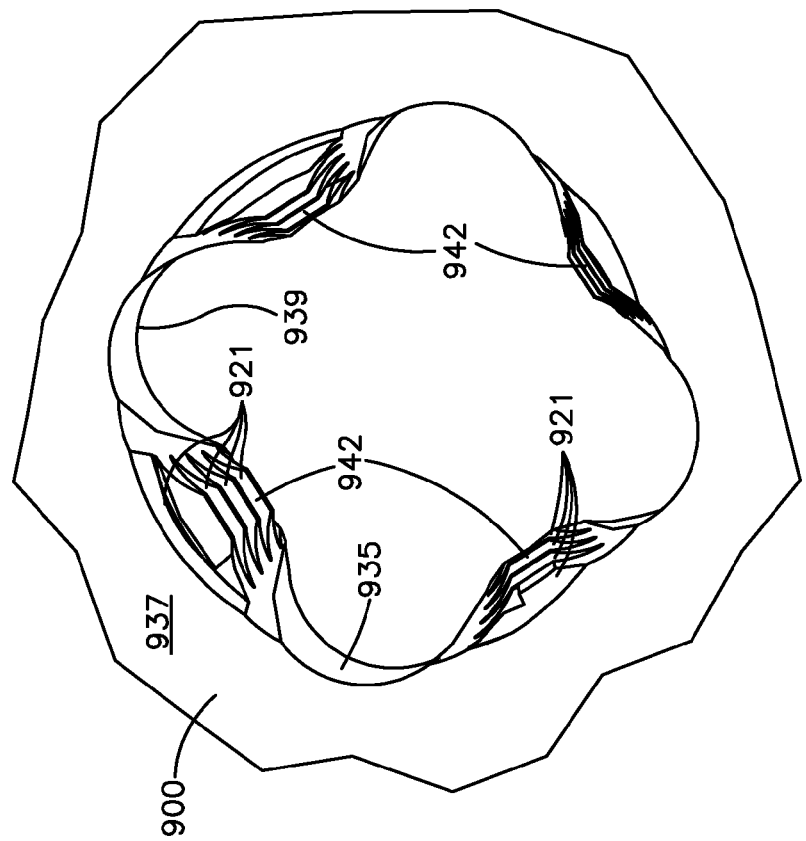
FIGS. 9A and 9B are perspective views of an embodiment of a bone plate hole according to the invention.
Figure 9A:
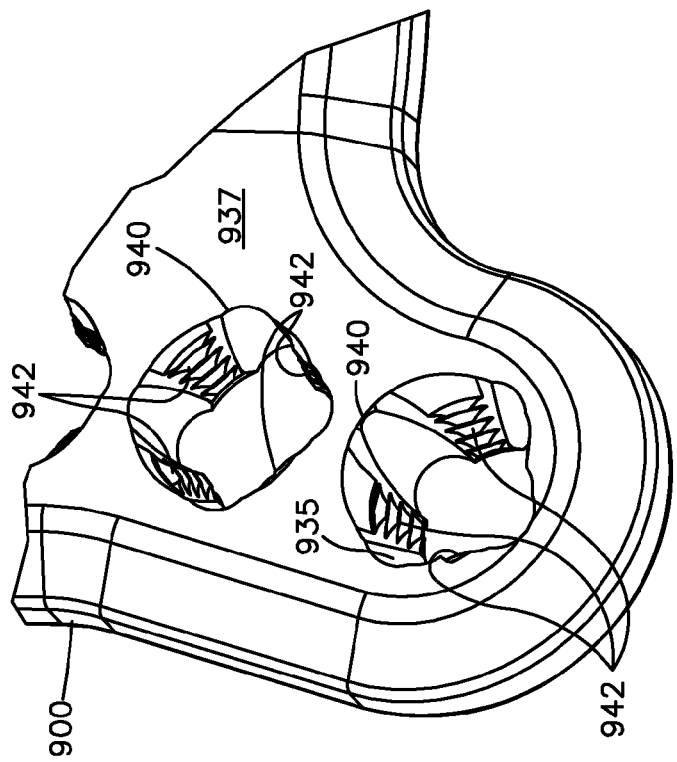
Figure 36:
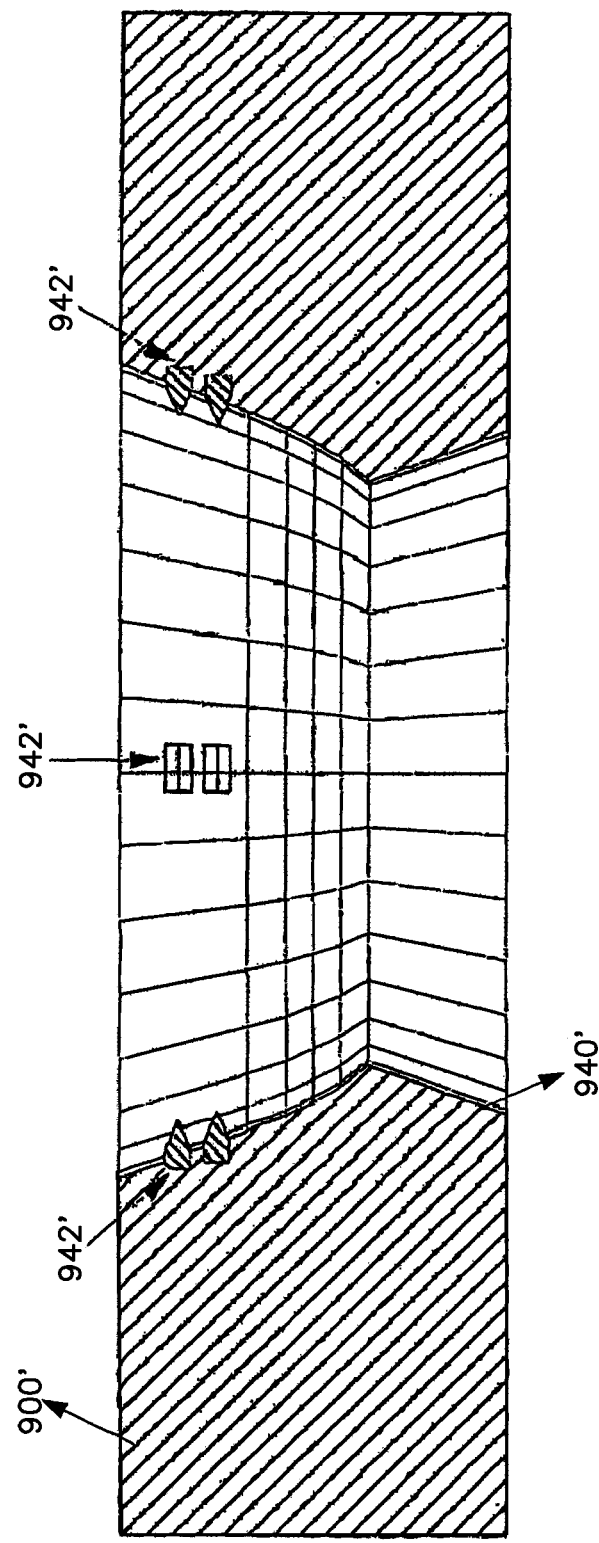
FIG. 36 is an enlarged front sectional view of a plate hole according to another embodiment of the present invention.

FIGS. 9A and 9B show bone plate 900 having bone plate holes 940 in accordance with the invention. Instead of a helical thread around the inner surface 935 of the plate holes as in conventional locking screw bone plate holes, bone plate holes of the invention have discrete, vertical columns 942 of protrusions which may preferably be thread segments arranged around the inner surface of the hole. The thread segment columns, if expanded to join each other (i.e. if extended completely around inner surface 935), would form a helical thread. The columns extend in a direction from upper surface 937 to lower surface 939 and are spaced preferably equidistantly apart around the inner surface of the hole. The number of thread segments 921 per column can vary depending on the surgical application and the dimensions of the bone plate and bone screw (e.g., plate thickness and thread pitch). However, each column should have at least two thread segments and preferably more to ensure a fixed angular relationship between the screw and the plate. In another embodiment as shown in FIG. 36, a bone plate 900' having a bone plate hole 940' may comprise protrusions 942' having peg or spike profiles. Specifically, the inner wall of each plate hole 940' may have a small number of isolated protrusions 942' numbering between 2 and 30 and designed to lock against a threaded spherical head of a screw (not shown) when the screw is driven in through the plate hole 940'. The protrusions 942' in the preferred embodiment are somehow flattened, having a width bigger than its length. In another embodiment, the protrusions 942' included on the inner wall of the plate hole 940' could be round instead of being flattened. Another variation could be related to the circular cross section of the protrusions 942' included on the inner wall of the plate hole 940' having the same width and length.

Note that instead of thread segments, columns 942 alternatively may have a plurality of teeth formed thereon. The columns of teeth, if expanded to join each other (i.e., if extended completely around inner surface 935), will not form a helical thread, but a series of concentric ridges and grooves perpendicular to the central axis of the bone plate hole. While such columns of teeth can also receive non-locking, locking, and variable-angle locking bone screws, the engagement of the teeth with the screwhead threads of the locking and variable-angle locking bone screws is less ideal than the engagement of thread segments with the screwhead threads of the locking and variable-angle locking bone screws.

Bone plate holes of the invention preferably have four columns 942 of thread segments, as shown in FIGS. 9A and 9B. However, bone plate holes of the invention alternatively may have other numbers of columns of thread segments.

Figure 10C:
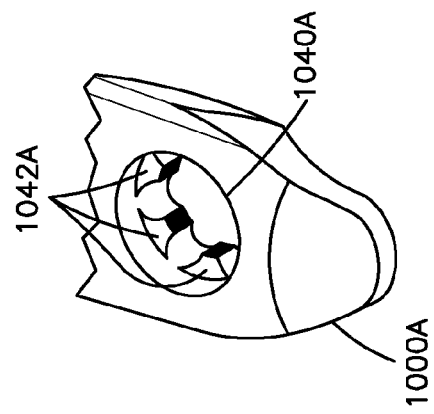
FIGS. 10A-C and 10D-F are top, cross-sectional, and perspective, respectively, of two similar embodiments of a bone plate hole according to the invention.
Figure 10F:
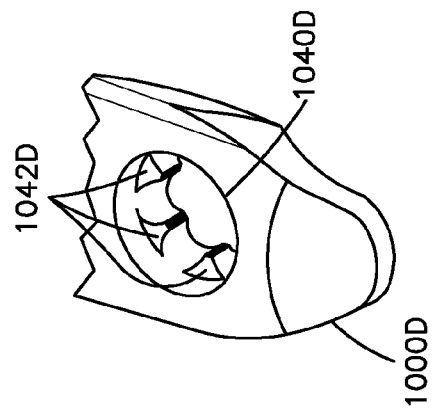
Figure 10B:
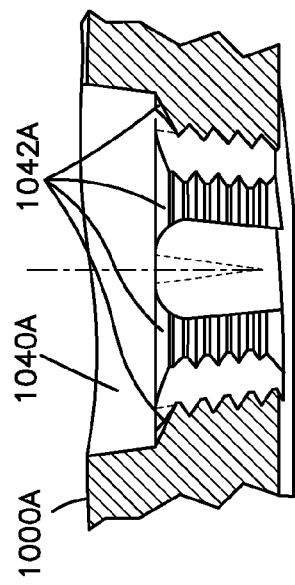
Figure 10E:
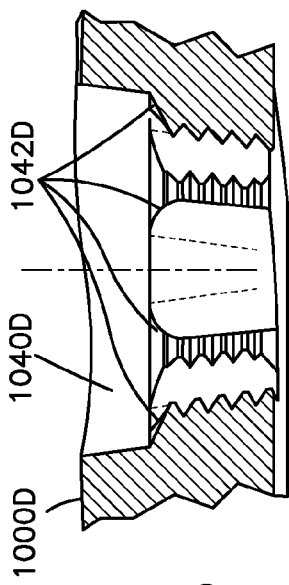
Figure 10A:
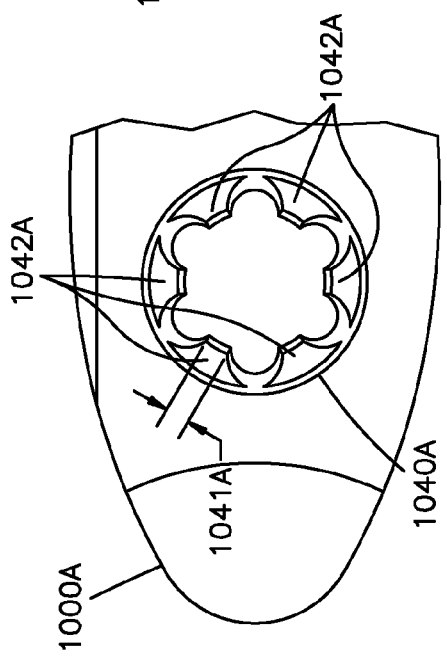
Figure 10D:
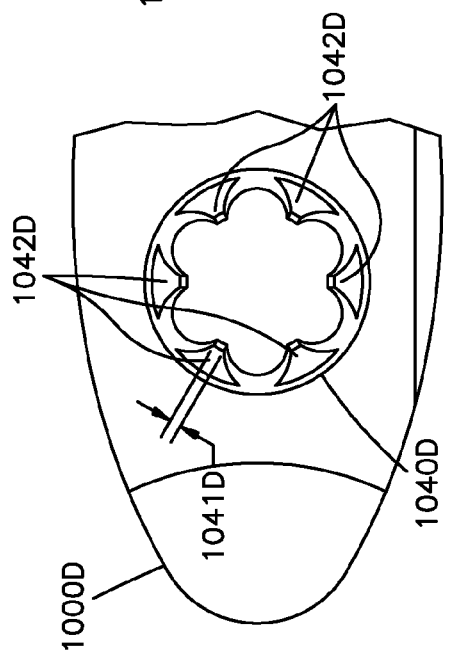

For example, as illustrated in the two embodiments of FIGS. 10A-C and 10D-F, respectively, bone plate holes 1040A and 1040D of respective bone plates 1000A and 1000D each have six columns of thread segments (note that because of the perspective shown, only three columns are visible in FIGS. 10C and 10F). The difference between thread segment columns 1042A and thread segment columns 1042D is that the column width 1041A of thread segments 1042A is about twice that of column width 1041D of thread segments 1042D. More than six columns of thread segments is not recommended, because of the increased risk of cross-threading the screwhead threads with the thread segment columns. Conversely, bone plate holes of the invention having fewer than three columns of thread segments is also not recommended because of the increased likelihood of insufficient stability at the bone/plate interface.

Figure 11:
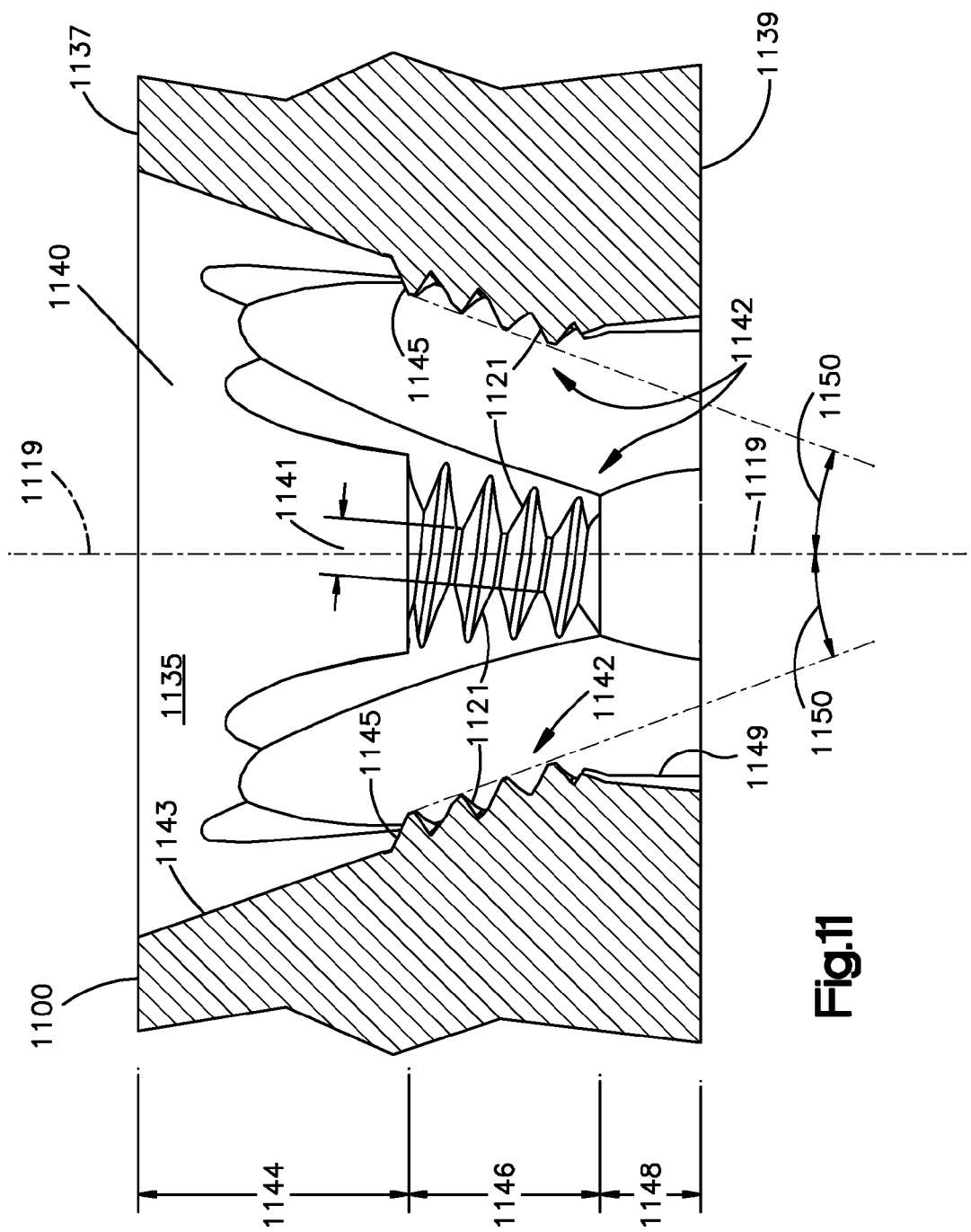
FIG. 11 is a cross-sectional view of a bone plate hole according to the invention.

FIG. 11 shows a cross-section of a bone plate hole according to the invention. Bone plate hole 1140 is formed in and extends completely through a bone plate 1100 from an upper surface 1137 to a lower bone-engaging surface 1139. Hole 1040 has an inner surface 1135 comprising a top portion 1144, a middle portion 1146, and a bottom portion 1148. Top portion 1144 extends from upper surface 1137 to middle portion 1146. Middle portion 1146 extends from top portion 1144 to bottom portion 1148 and preferably has the smallest diameter of the hole. And bottom portion 1148 extends from middle portion 1146 to lower surface 1139. Top portion 1144 is unthreaded, has a preferably smooth inner surface 1143, and is preferably conically tapered inward toward the lower surface. Bone plate hole 1140 has a shoulder 1145 at the intersection of top portion 1144 and middle portion 1146 (which is the top of the first thread segment in each column). Shoulder 1145 may serve as a stop for the screwhead of a non-locking bone screw inserted through hole 1140 and, in one embodiment, is angled such that it forms an angle of about 60 degrees with the central axis of the hole. Note that inner surface 1143 or upper surface 1137 may serve as a stop for the screwhead of a non-locking bone screw depending on the size and shape of the head. Bottom portion 1148 also has a preferably smooth inner surface 1149 and is preferably tapered inward toward the upper surface in the form of an undercut sphere. In one embodiment of the invention, the radius of the undercut sphere is about 1.75 mm. For a bone plate thickness of about 2 mm, for example, the top portion may extend about 1 mm and the middle and bottom portions each may extend about 0.5 mm.

In this embodiment, middle portion 1146 of bone plate hole 1140 has four discrete columns of thread segments 1142 on inner surface 1135. Each column 1142 is preferably inclined inward toward lower surface 1139 at an angle 1150 measured with respect to the central axis 1119. In one embodiment, angle 1150 is preferably about 15 degrees. Each column 1142 also preferably has four or five thread segments 1121. Other embodiments may have more or less thread segments as described above. For a bone plate hole accommodating a 2.4 mm variable-angle locking screw, the column width 1141 of each thread segment is preferably about 0.35 mm. Other embodiments may have other column widths, depending on the application.

Figure 12:
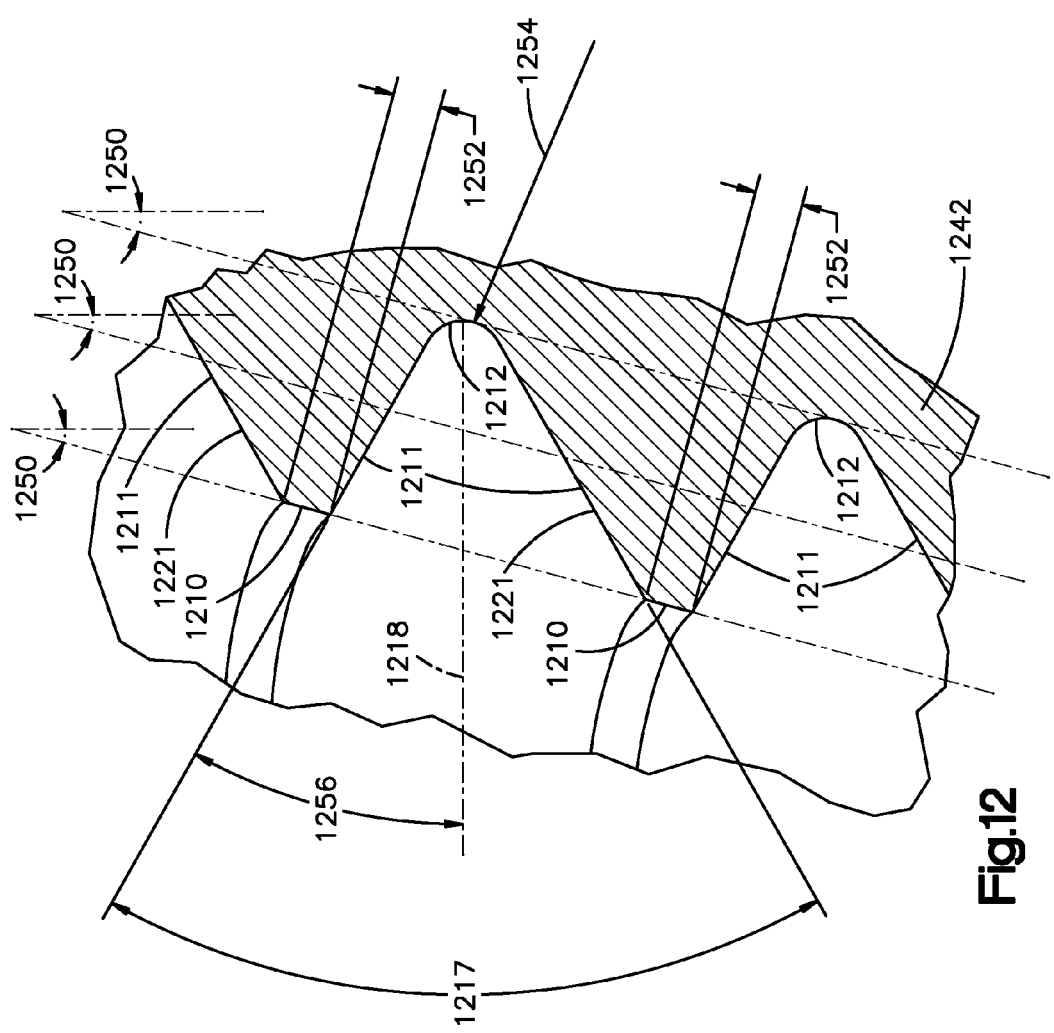
FIG. 12 is an enlarged, partial cross-sectional profile view of a column of thread segments of the bone plate hole of FIG. 11.

FIG. 12 shows a cross-sectional profile of a portion of a column 1242 of thread segments 1221. (Note that a cross-sectional profile of an alternative column of teeth, as described above, appears the same as the thread segments.) In FIG. 12, two of the five thread segments 1221 of column 1242 are shown. Column 1242 of thread segments is preferably inclined toward the lower surface of the bone plate at angle 1250. In one embodiment, angle 1250 is about 15 degrees. As seen in profile, column 1242 of thread segments 1221 includes peaks (or crests) 1210 and troughs (or roots) 1212 connected to each other by flanks 1211 at thread angles 1217. Peaks 1210 preferably have a length 1252, which in one embodiment is about 0.04 mm. Troughs 1212 preferably have a radius 1254, which in one embodiment is about 0.03 mm. Angle 1217 is preferably about 60 degrees, and the bisection of troughs 1212, as represented by trough profile line 1218, occurs at an angle 1256 of preferably about 30 degrees as measured from a flank 1211. Other embodiments of bone plate hole thread-segment columns alternatively may have other values of column incline angle, peak lengths, trough radiuses, thread angles, and bisection angles (which are a function of thread angle).

Figure 13:
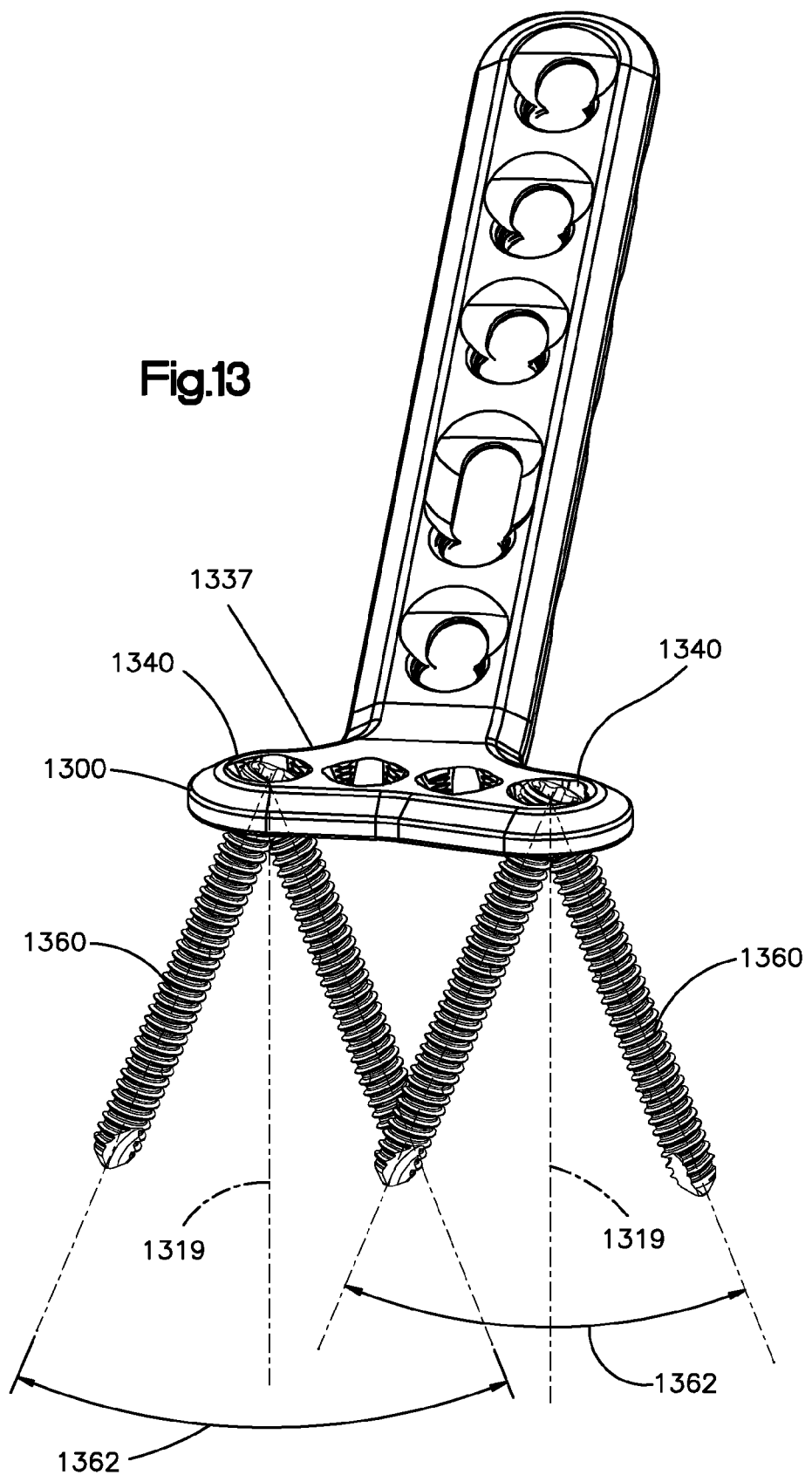
FIG. 13 is a perspective view of an embodiment of a bone plate system the range of selectable angles of a variable-angle locking screw according to the invention.

Advantageously, variable-angle locking bone screws of the invention can be driven into bone and secured to the bone plate at a selectable angle within a range of selectable angles. FIG. 13 shows an embodiment of the invention in which bone plate 1300 has bone plates holes 1340 constructed in accordance with the invention. Each hole 1340 can advantageously receive a variable-angle locking screw 1360, also constructed in accordance with the invention, at a selectable angle in any direction within a range of angles. The range of angles forms a cone having an angle 1362, which in this embodiment is about 30 degrees. In other words, variable-angle locking screw 1360 can be inserted into a hole 1340 and secured to bone plate 1300 at a selectable angle ranging from 0 degrees to 15 degrees in any direction with respect to central axis 1319 of bone plate 1340.

FIGS. 14A-17B show an advantageous feature of a bone plate hole constructed in accordance with the invention. Bone plate 1400 has at least three bone plate holes 1440. Each hole 1440 has four columns of thread segments 1542 and can advantageously receive any one of a non-locking, locking, or variable-angle locking bone screw.

Figure 14A:
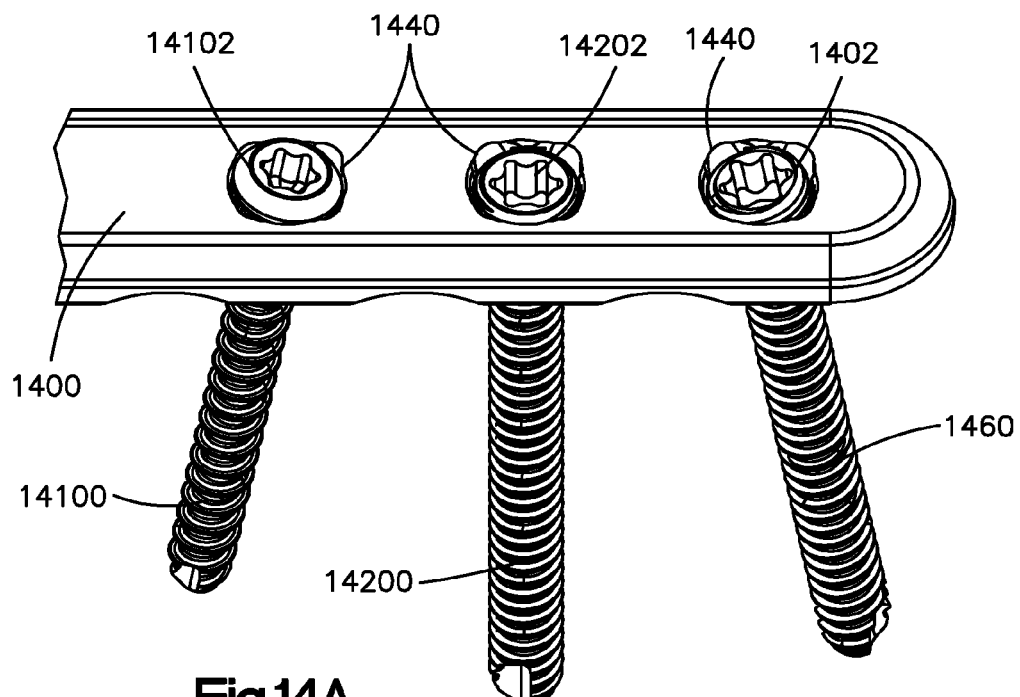
FIGS. 14A and 14B are perspective and elevational front views, respectively, of an embodiment of a bone plate system showing non-locking, locking, and variable-angle screws used with a bone plate according to the invention.
Figure 14B:
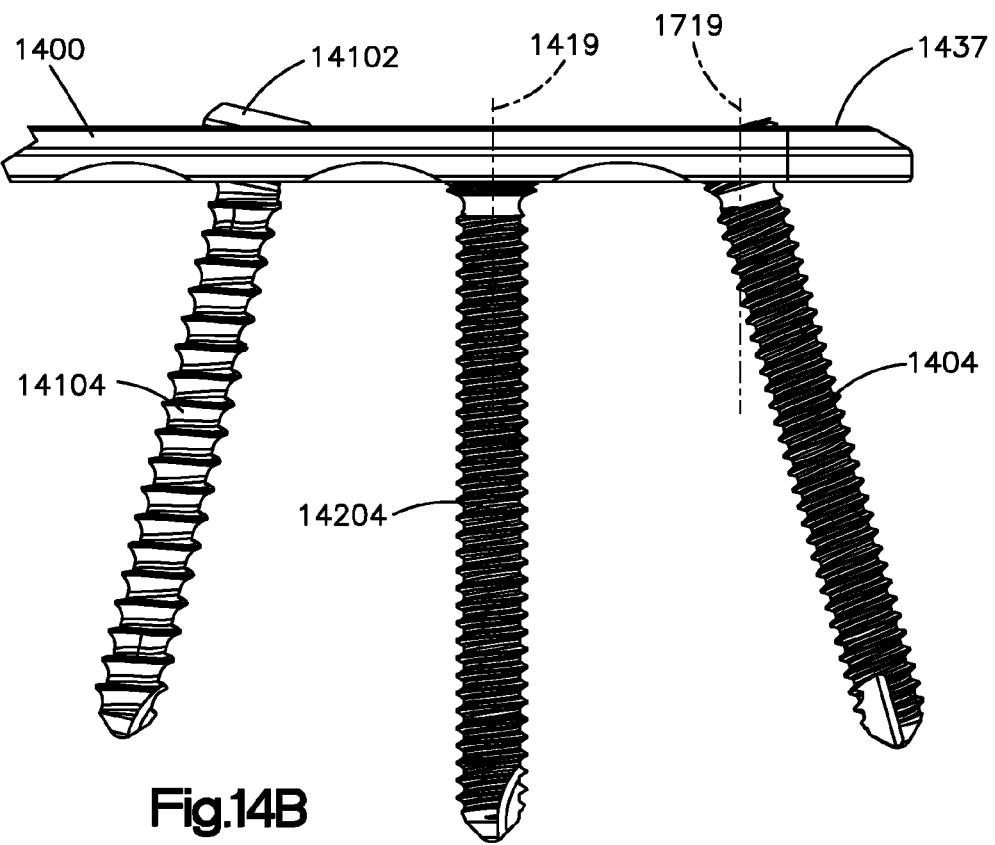
Figure 15A:
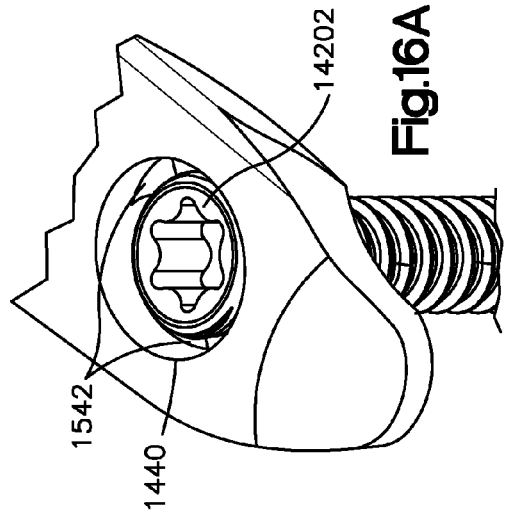
FIGS. 15A and 15B are perspective and elevational front views, respectively, of a non-locking screw inserted through a bone plate hole according to the invention.
Figure 15B:
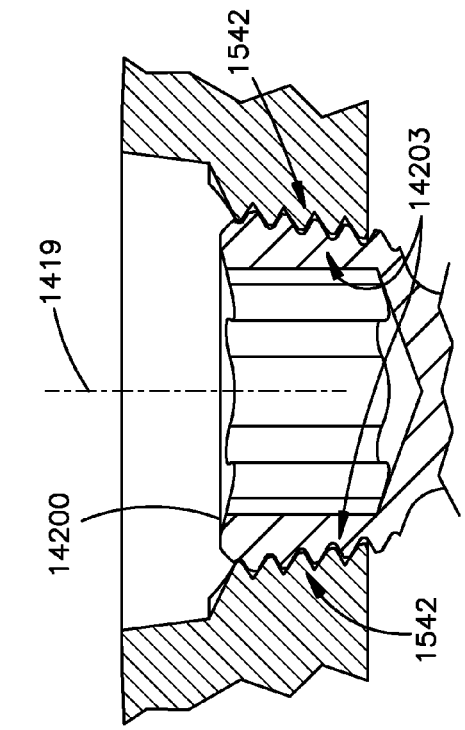
Figure 16A:
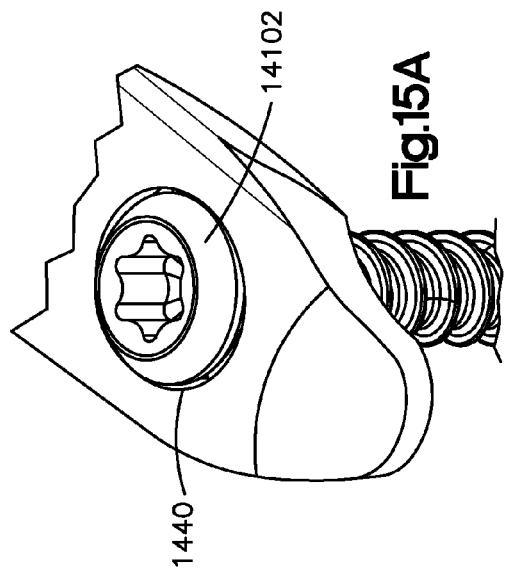
FIGS. 16A and 16B are perspective and elevational front views, respectively, of a locking screw driven into a bone plate hole according to the invention.
Figure 16B:
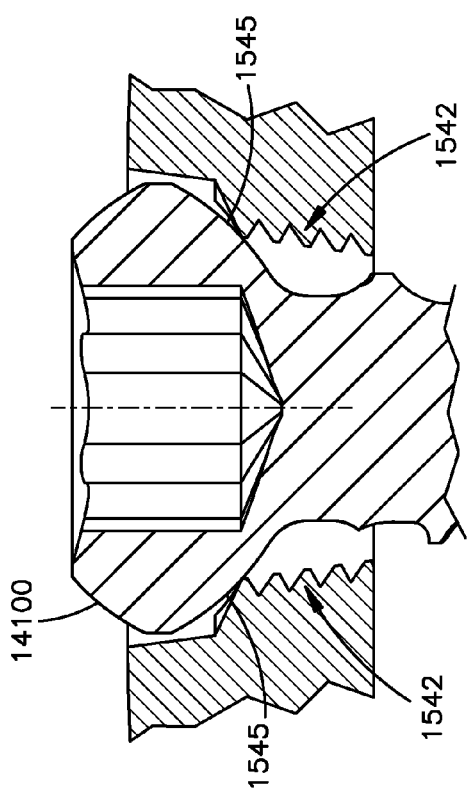

As shown in FIGS. 14A, 14B, 15A, and 15B, a conventional non-locking bone screw 14100 can be inserted through one of bone plate holes 1440. Non-locking bone screw 14100 has a non-threaded screwhead 14102 and a threaded shank 14104, each appropriately sized and configured for use with hole 1440. Note that non-locking bone screw 14100 does not have to be inserted through hole 1440 coaxially with the central axis of the hole, but may instead be inserted through hole 1440 at a selectable angle, as shown in FIG. 14B. FIG. 15B shows that screwhead 14102 does not engage the columns of thread segments 1542, but instead contacts shoulder 1545 of hole 1440 when fully seated therein.

FIGS. 14A, 14B, 16A, and 16B show conventional locking bone screw 14200 inserted though a second bone plate hole 1440. Locking bone screw 14200 has a screwhead 14202 with a thread 14203 on an outer surface therefore. Both the screwhead and thread are appropriately sized and dimensioned such that thread 14203 can threadingly engage and mate with columns of thread segments 1542. In order to properly engage and mate with columns of thread segments 1542, locking bone screw 14200 should be inserted through hole 1440 coaxially with central axis 1419 of the hole. Screw 14200 also has a threaded shank 14204 for engaging bone. Shank 14204 is also appropriately sized and dimensioned for insertion through hole 1440.

FIGS. 14A, 14B, 17A, and 17B show variable-angle locking bone screw 1460 inserted through a third bone plate hole 1440. Variable-angle locking bone screw 1460, constructed in accordance with the invention, has a threaded shank 1404 and a partially-spherical head 1402 with thread 1403 on an outer surface thereof. Screwhead thread 1403 has a profile that advantageously follows the arc-shaped (i.e., non-linear) radius of curvature of the spherically-shaped portion of head 1402. Screw 1460 is shown inserted into the third hole 1440 non-coaxially with the central axis 1719 with thread 1403 securely engaging columns of thread segments 1542.

FIGS. 18A-24C illustrate various features of an embodiment of a bone plate hole according to the invention. Other than the formation of columns around the inner surface of the hole, at least some of these features need not be used in alternative embodiments of a bone plate hole according to the invention. Also note that the order in which these features are described and shown does not imply the order or steps of a particular process for fabricating a bone plate hole of the invention. As is apparent to those of ordinary skill in the art, there is more than one way in which holes of the invention can be fabricated.

Figure 18A:
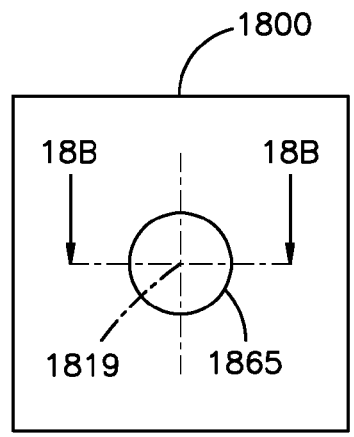
FIGS. 18A,B,C-23A,B,C are top, cross-sectional, and perspective views, respectively, of various features of a bone plate hole according to the invention.
Figure 18B:
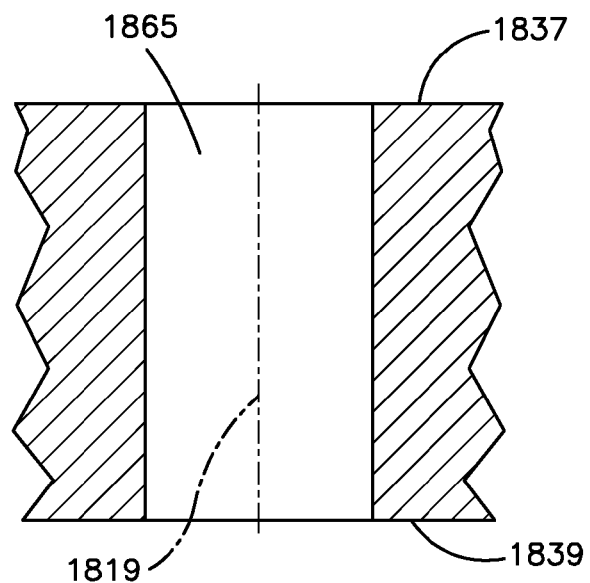
Figure 18C:
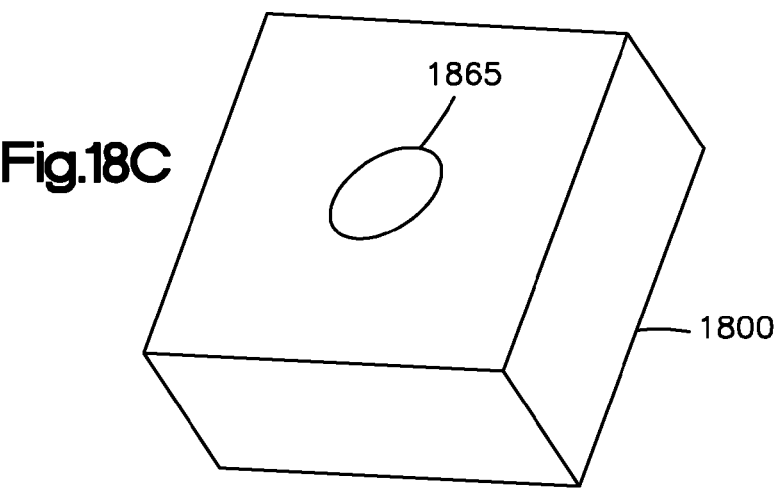

A bone plate hole of the invention typically starts with a circular start hole 1865, as shown in FIGS. 18A-C. Start hole 1865 has a central axis 1819 and extends completely through a bone plate 1800 from upper surface 1837 to lower surface 1839. In one embodiment, the diameter of the start hole is about 2.2 mm.

FIGS. 19A-C show an inner surface profile of a bone plate hole without other features. The profile of hole 1965 in bone plate 1900 includes an inwardly tapering top portion 1944, a protruding, inwardly tapering middle portion 1946, and a spherically undercut bottom portion 1948. In one embodiment, the middle and bottom portions of the hole each extend along the central axis 1919 by about 1 mm, and the radius of the spherical undercut is about 1.75 mm.

Figure 20A:
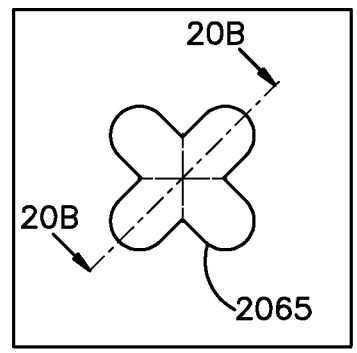
Figure 20B:
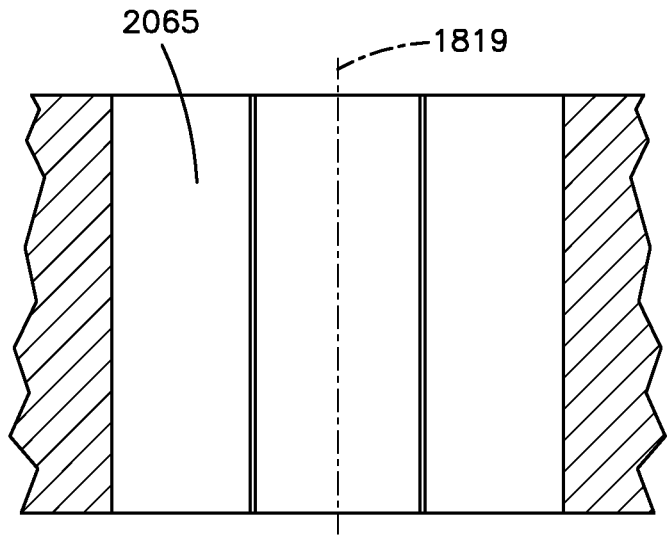
Figure 20C:
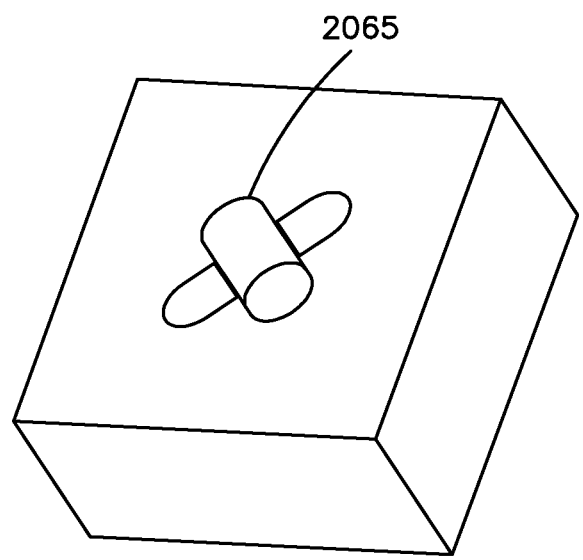

Another feature is an optional "X key" cutout 2065, shown in FIGS. 20A-C. X key cutout 2065 is preferably pressed, cut, or stamped completely through the bone plate about the same central axis 1819 as start hole 1865. In one embodiment, each leg of the "X" has a width of about 1.5 mm and terminates in an arc-shape having a radius of about 0.75 m. In this same embodiment, the span between the ends of collinear legs is about 4.25 mm. The X key cutout forms a cloverleaf design intended to accommodate a drill guide having a complementary drill-guide tip design, as described further below with respect to FIGS. 25A-27D.

Figure 21A:
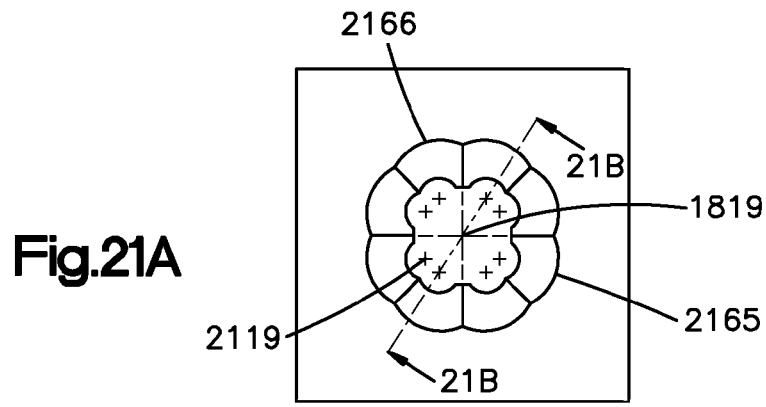
Figure 21B:
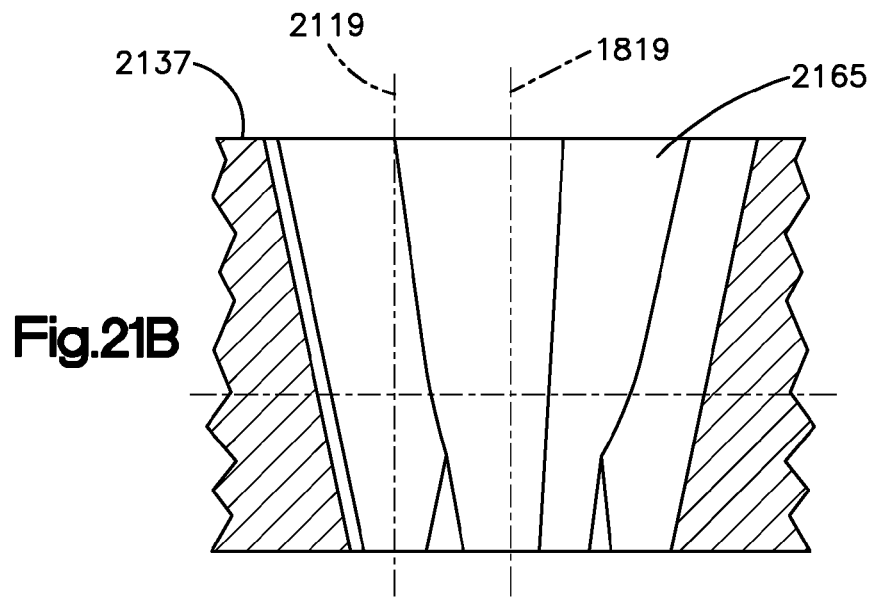
Figure 21C:
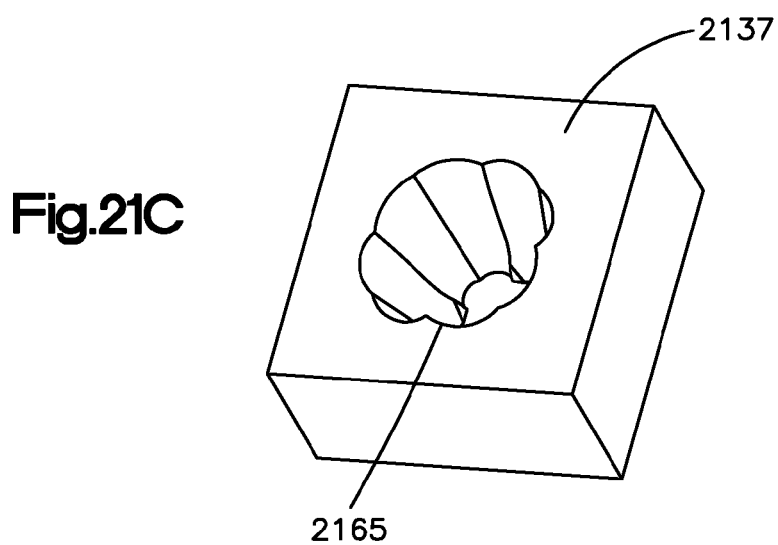

Another feature is a preferably 12-degree relief cut 2165, as shown in FIGS. 21A-C (without any other hole features). Relief cut 2165 includes eight symmetrically cut sections 2166, two sections per quadrant, in which each section inclines inward at about 12 degrees from the upper surface 2137 of the bone plate. The relief cut is made completely through the bone plate. In one embodiment, each relief cut axis 2119 is about 1.1 mm from central axis 1819 of the bone plate hole.

Figure 22A:
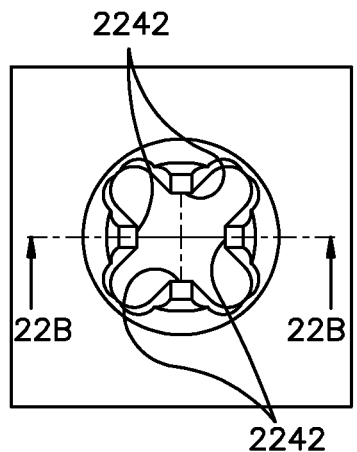
Figure 22B:
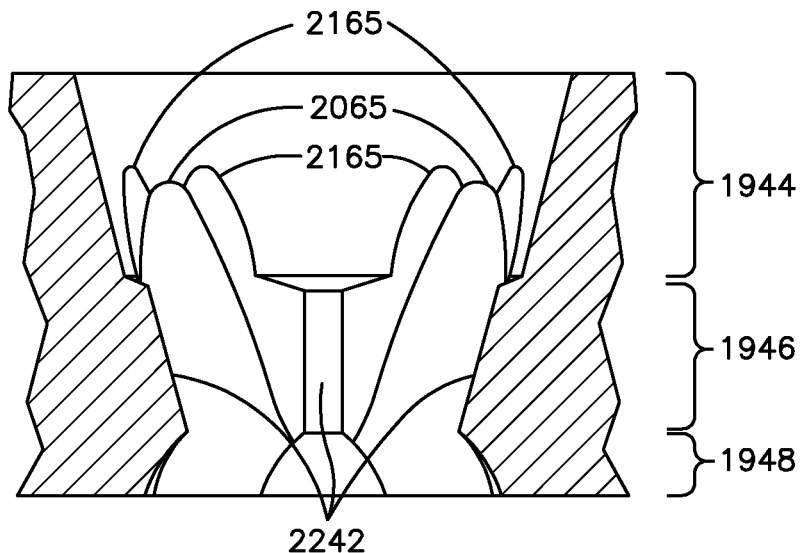
Figure 22C:
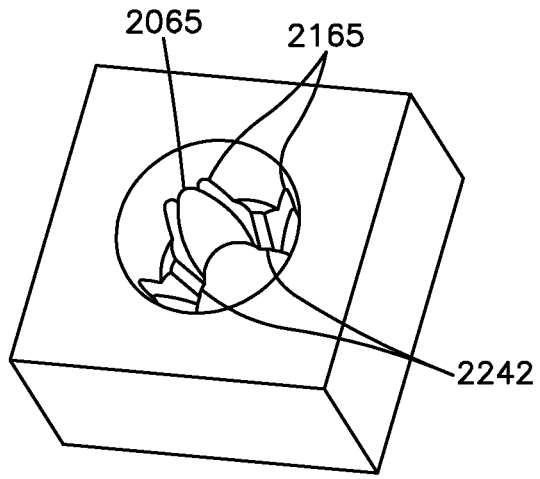

FIGS. 22A-C show a hole profile with top portion 1944, middle portion 1946, bottom portion 1948, X key cutout 2065, relief cut 2165, and four columns 2242 formed therein that have not yet had teeth or thread segments cut into them. Columns 2242 are formed by removing axial sections from the inner surface of the middle portion of the hole.

Figure 23A:
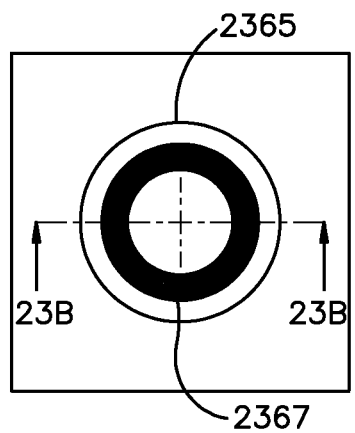
Figure 23B:
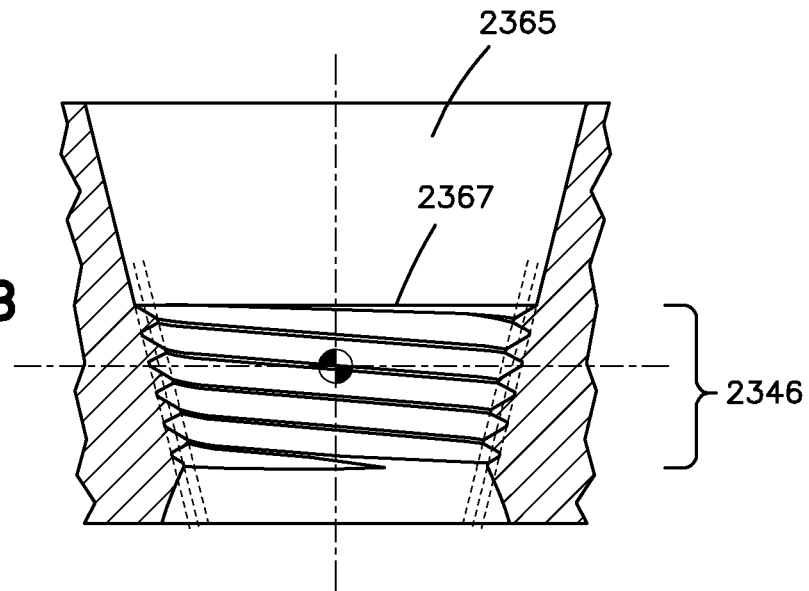
Figure 23C:
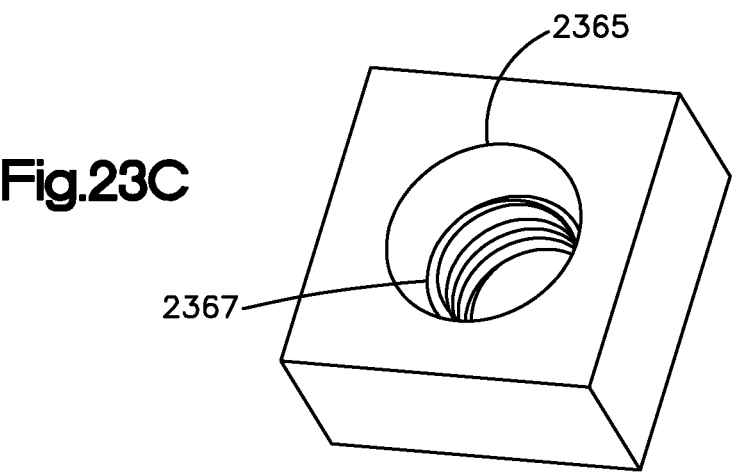

A thread cutting process forms the thread segments in columns 2242. Note that if middle portion 1946 had not had the columns formed therein, the thread cutting process would have cut a helical thread 2367 in and completely around the inner surface of middle portion 2346 of hole 2365 as shown in FIGS. 23A-C. The thread profile (i.e., the peaks, troughs, flanks, and the angles formed by adjacent flanks) of the thread segments is preferably the same as the profile described above for the columns of thread segments shown in FIGS. 11 and 12.

As described previously, instead of forming thread segments in columns 2242, teeth may be formed alternatively therein. Teeth are formed by cutting grooves in the column that are perpendicular, or at least substantially perpendicular, to the central axis of the hole. Note that if middle portion 1946 had not had the columns formed therein, the groove cutting process would have formed a concentric, parallel series of alternating grooves and ridges.

Figure 24A:
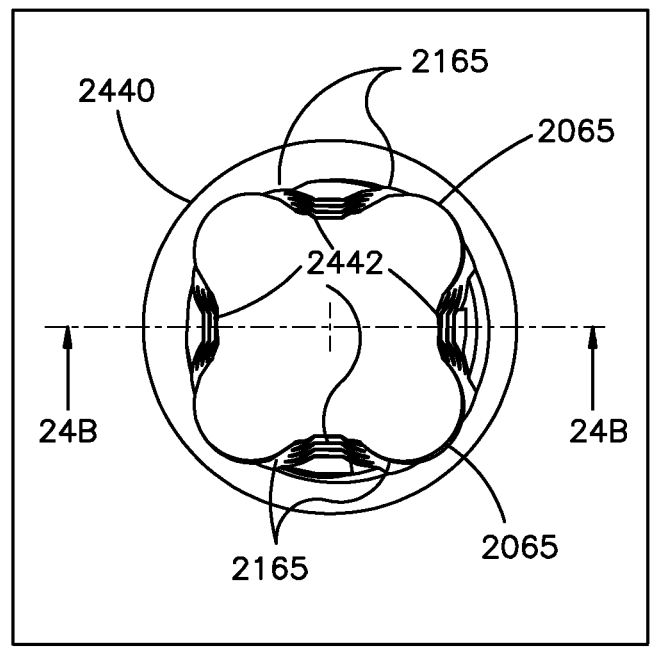
FIGS. 24A-D are top, cross-sectional, top perspective, and bottom perspective views, respectively, of a bone plate hole according to the invention.
Figure 24B:
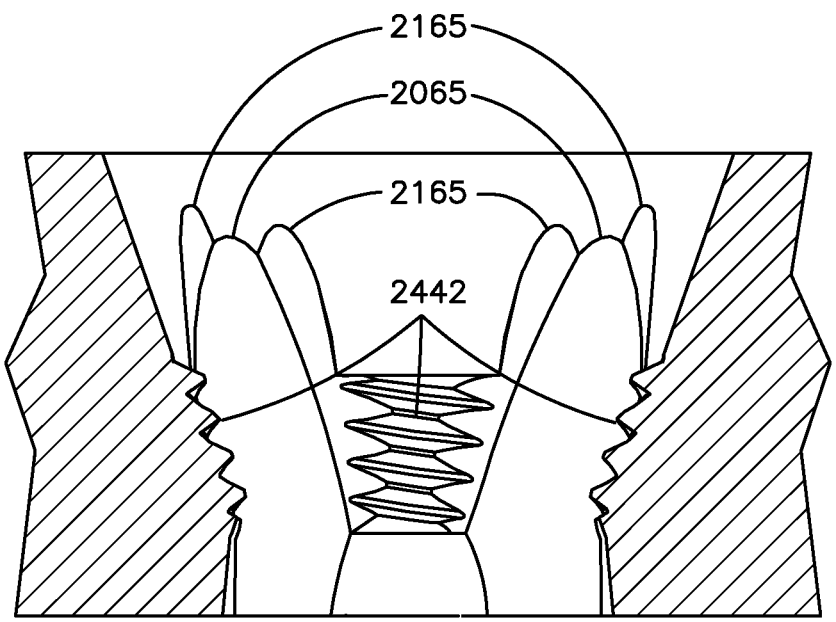
Figure 24D:
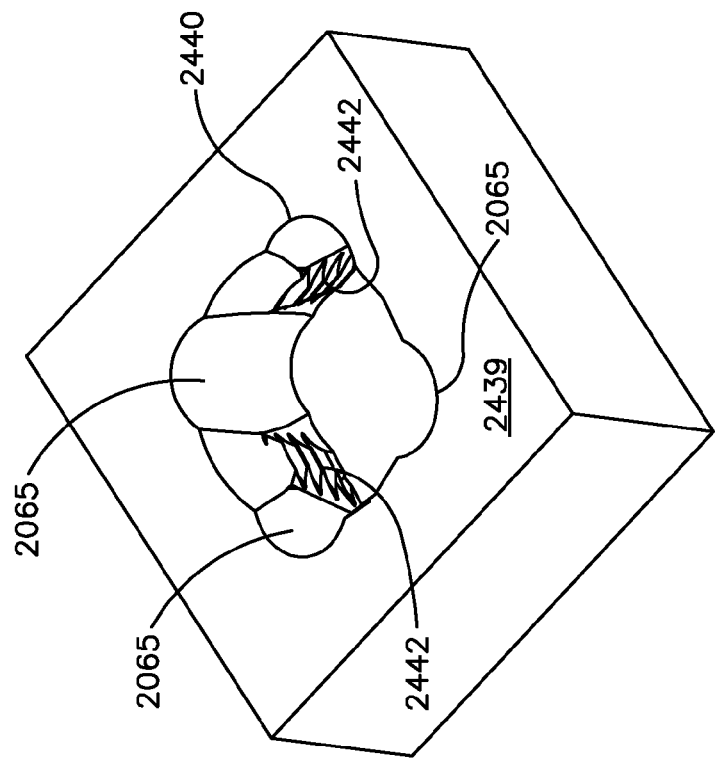
Figure 24C:
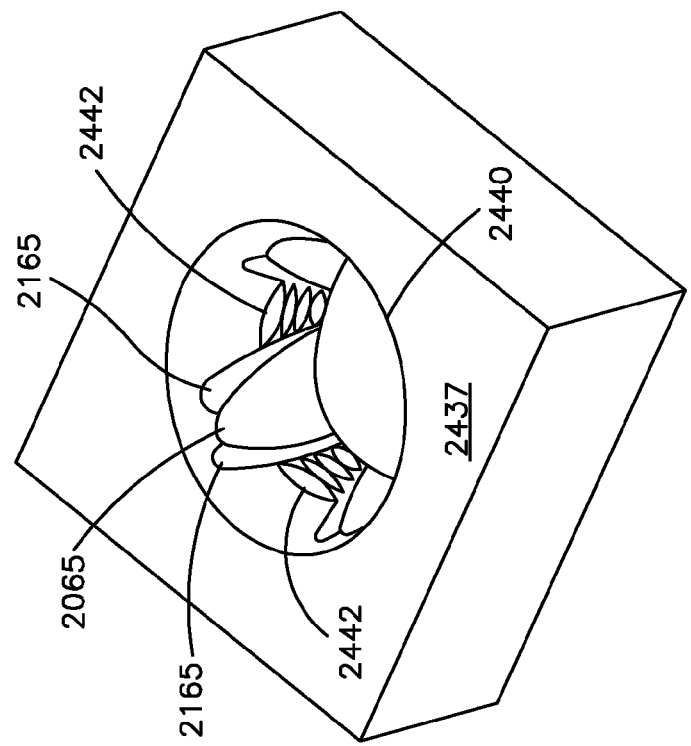

FIGS. 24A-D show a completed embodiment of a bone plate hole according to the invention. Hole 2440 includes columns of thread segments 2442, X key cutout 2065, and relief cut 2165. FIG. 24C shows top surface 2437 of hole 2440, while FIG. 24D shows bottom surface 2439 of hole 2440 that is intended to contact, be adjacent to, or face the bone.

FIGS. 25A-27D show another advantageous feature of the invention in connection with drill guides. One embodiment of a drill guide constructed in accordance with the invention is shown in FIGS. 25A-26C, and another embodiment is shown in FIGS. 27A-D.

Figure 25C:
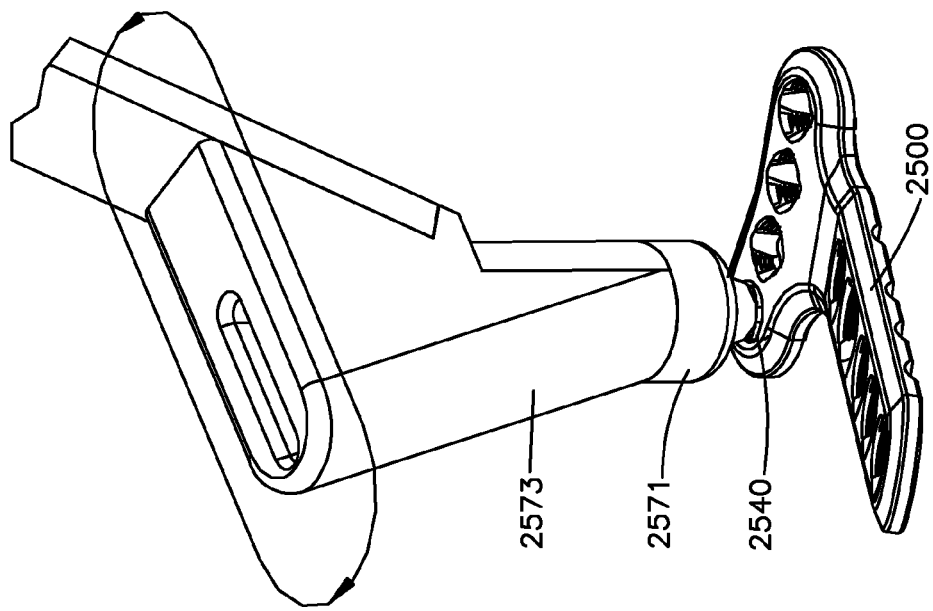

FIG. 25A shows drill guide 2570, which has a tip 2571 and a handle 2573. As shown in FIG. 25B, tip 2571 has four equidistantly spaced and rounded wings or sections 2572 forming a cloverleaf design arranged around a drill shaft for guiding a drill, a bone screw, and/or a driving/extracting tool through a bone plate 2500 and into bone at a selectable angle. Wings 2572 are sized and configured to fit snugly within the X key cutouts 1965 of bone plate holes 2540. This allows drill guide 2570 to be inserted coaxially into a bone plate hole 2540 (i.e., coaxially with the central axis of a bone plate hole) and to be easily held in place while a hole is drilled into the bone and/or a bone screw is driven into the bone. Note that, alternatively, configurations other than the cloverleaf design and X key cutouts can be used for tip 2571 and holes 2540, respectively. As shown in FIG. 25C, handle 2573 can swivel 360 degrees about tip 2571 and the central axis of the hole 2540 in which tip 2571 is inserted.

Figure 26A:
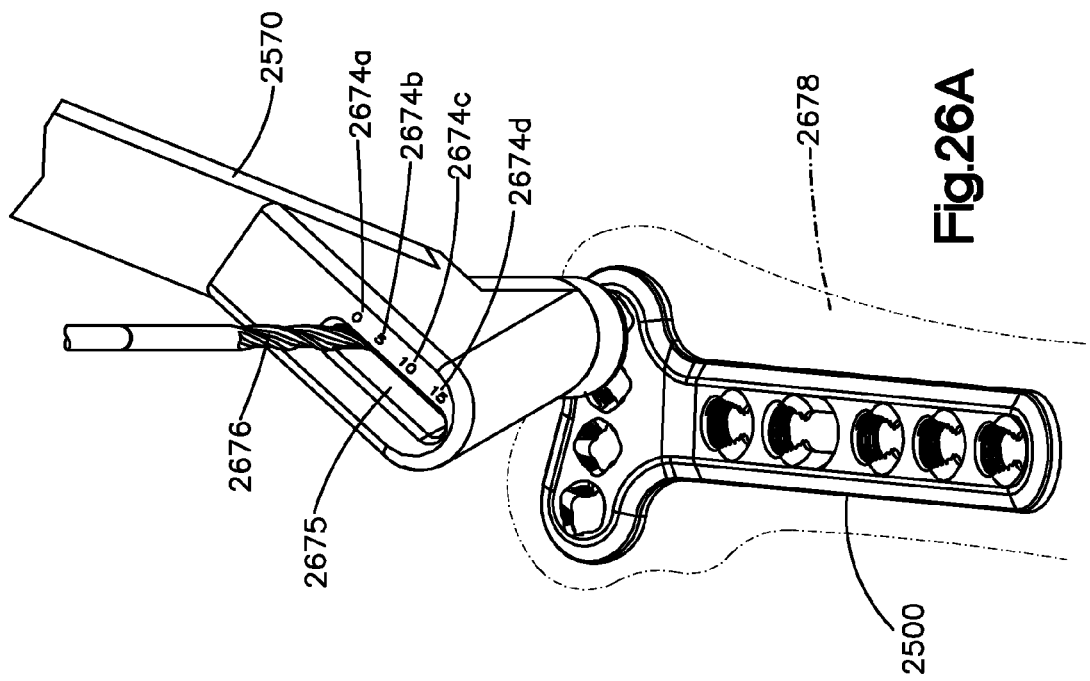

FIG. 26A shows drill guide 2570 having a slot 2675 through which drillings within a range of selectable angles can be made. In this embodiment, the selectable angles range from 0 degrees to 15 degrees. The ability of handle 2573 to swivel 360 degrees thus provides a 30 degree cone of angulation around the central axis of the hole. Drill guide 2570 has markings 2674a-d along slot 2675, which in this embodiment indicate 0, 5, 10, and 15 degrees, respectively, with respect to the central axis of the hole. Other embodiments may have other angle ranges and/or other markings of selectable angles. FIGS. 26A and 26B show a drill bit 2676 being guided through drill guide 2570, through bone plate 2500, and into bone 2678 at the uppermost angle setting 2674a, which in this embodiment is 0 degrees with respect to the central axis of the bone plate hole (i.e., coaxial). FIG. 26C shows drill bit 2676 being guided through drill guide 2570, through bone plate 2500, and into bone 2678 at the lowermost angle setting 2674d, which in this embodiment is 15 degrees with respect to the central axis of the bone plate hole or 75 degrees with respect to the top surface 2637 of bone plate 2500.

FIGS. 27A-D show another embodiment of a drill guide in accordance with the invention. Drill guide 2770 has a funnel-shaped guide 2777 with a tip 2771A at one end, a coaxial guide 2779 with a tip 2771B at the opposite end, and a handle 2773 there between. Tips 2771A and 2771B each have four equidistantly spaced and rounded wings or sections 2772 forming a cloverleaf design around a drill shaft for guiding a drill, a bone screw, and/or a driving/extracting tool 2776 through a bone plate and into bone. Wings 2772 are sized and configured to fit snugly within the X key cutouts 1965 of bone plate holes of the invention (e.g., bone plate holes 2540). This allows either end of drill guide 2770 to be inserted coaxially into a bone plate hole (i.e., coaxially with the central axis of the bone plate hole) and to be easily held in place while a hole is drilled into bone and/or a bone screw is driven into bone. Note that, alternatively, configurations other than the cloverleaf design and X key cutouts can be used for tips 2771A and 2771B and holes of the invention, respectively. Unlike handle 2573 of drill guide 2570, handle 2773 does not swivel about either tip 2771A or 2771B. Instead, funnel-shaped guide 2777 has a funnel-shaped bore 2775 extending there through and centered about the central axis of the bone plate hole in which tip 2771A is inserted. Bore 2775 provides a cone of angulation, which in this embodiment is 30 degrees. With funnel-shaped guide 2777 inserted in a bone plate hole of the invention, and thus locked in a fixed position, drillings can be advantageously made at a selectable angle in any direction ranging from 0 degrees to 15 degrees with respect to the central axis of the hole. At the opposite end of drill guide 2770, coaxial guide 2779 has bore 2778 extending there through. With coaxial guide 2779 inserted in a bone plate hole of the invention, bore 2778 can be used to guide a drill bit or driving/extracting tool 2776 coaxial to the central axis of the hole. Coaxial guide 2779 also has an optional measurement gauge 2774 to help determine penetration depths.

Figure 28:
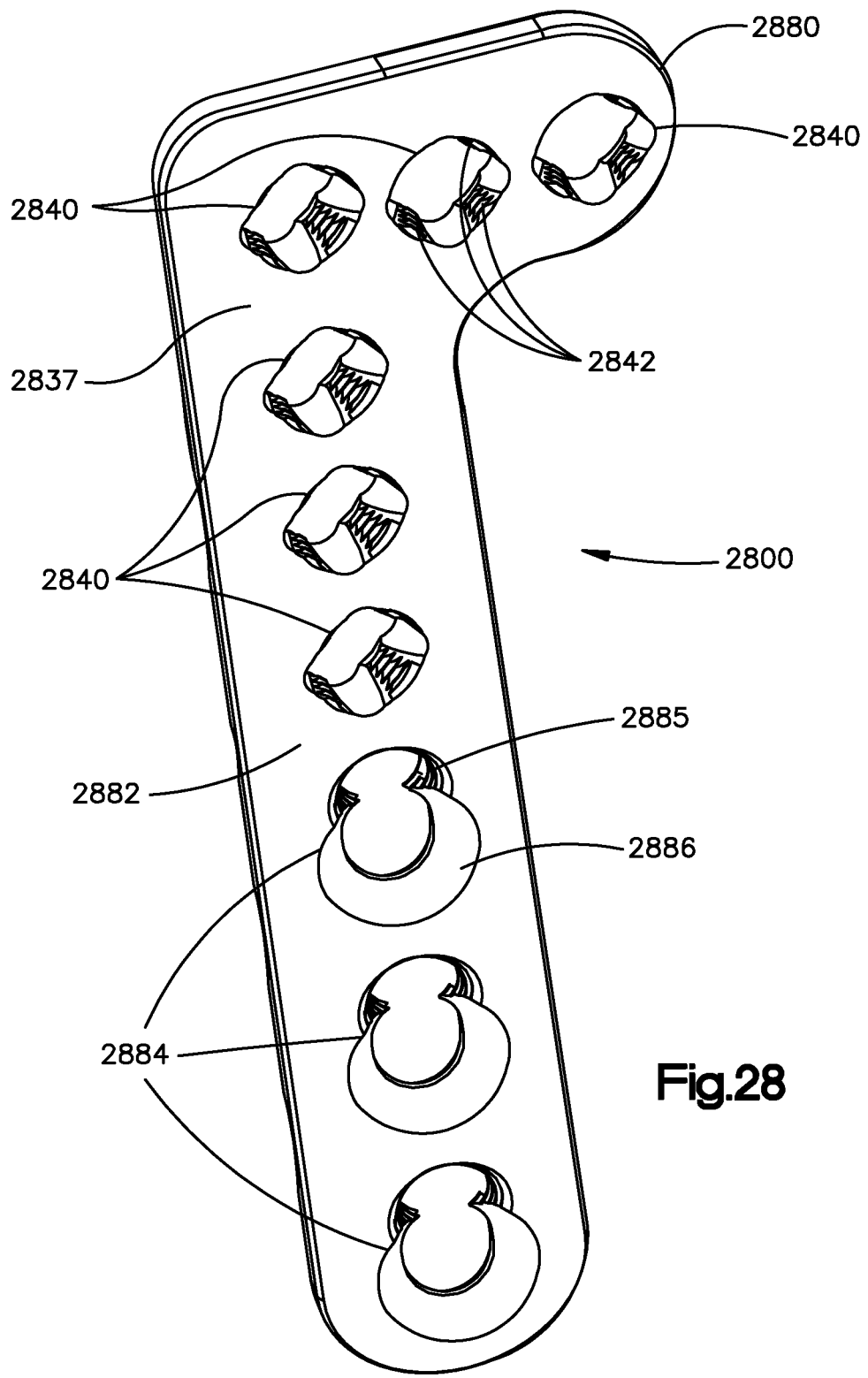
FIG. 28 is a perspective view of an embodiment of a bone plate according to the invention.

FIG. 28 shows a bone plate configuration in accordance with the invention. Bone plate 2800 is shaped and configured for, but not limited to, fractures of the lateral proximal tibial plateau. Bone plate 2800 has a head portion 2880 configured and dimensioned to conform to the metaphysis of the lateral proximal tibia, and a shaft portion 2882 configured and dimensioned to conform to a diaphysis of the lateral proximal tibia. Bone plate 2800 further has an upper surface 2837 and a plurality of bone plate holes 2840 that extend completely through the bone plate, from upper surface 2837 to the bottom surface. Each hole 2840 has four columns of thread segments 2842 and can advantageously receive either a non-locking, locking, or variable-angle locking bone screw according to the invention. Shaft portion 2882 also has several figure-eight shaped combination holes 2884 for increased versatility, where one portion 2885 of the figure-eight has preferably four columns of thread segments and the other portion 2886 is preferably smooth and unthreaded. Portion 2886 can receive a non-locking bone screw, while portion 2885 can advantageously receive either a non-locking, locking, or variable-angle locking bone screw. The ability to use variable-angle locking screws in shaft portion 2882 is particularly useful when the far cortex of part of the diaphysis is missing or severely damaged since fixation with non-locking screws is problematic because of the condition of the far cortex. The particular type and placement of bone plate holes may of course vary.

Figure 29A:
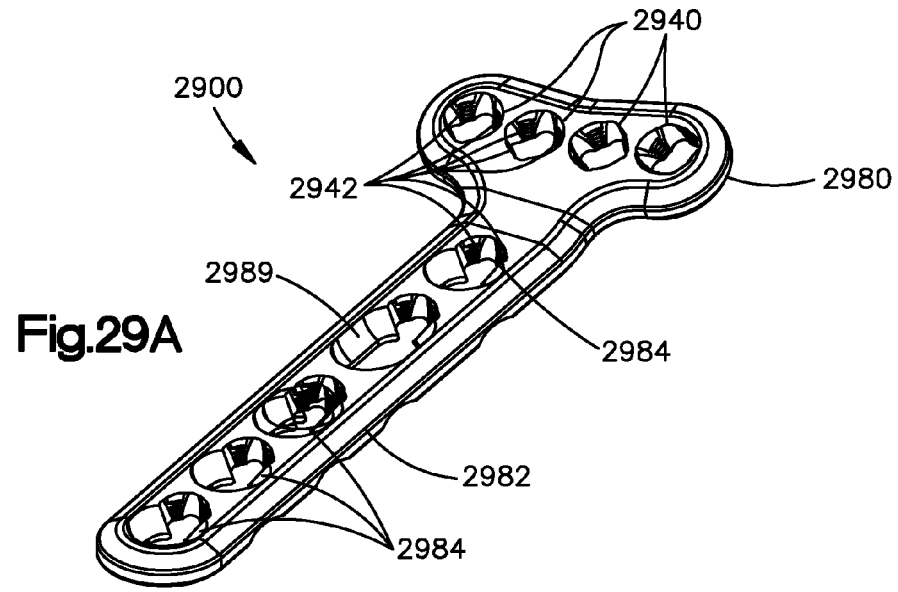
FIGS. 29A-C are perspective, front elevational, and top views, respectively, of another embodiment of a bone plate according to the invention.
Figure 29B:
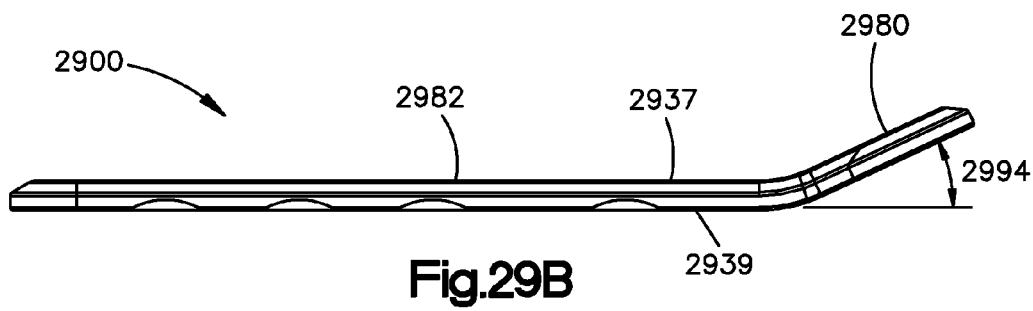
Figure 29C:
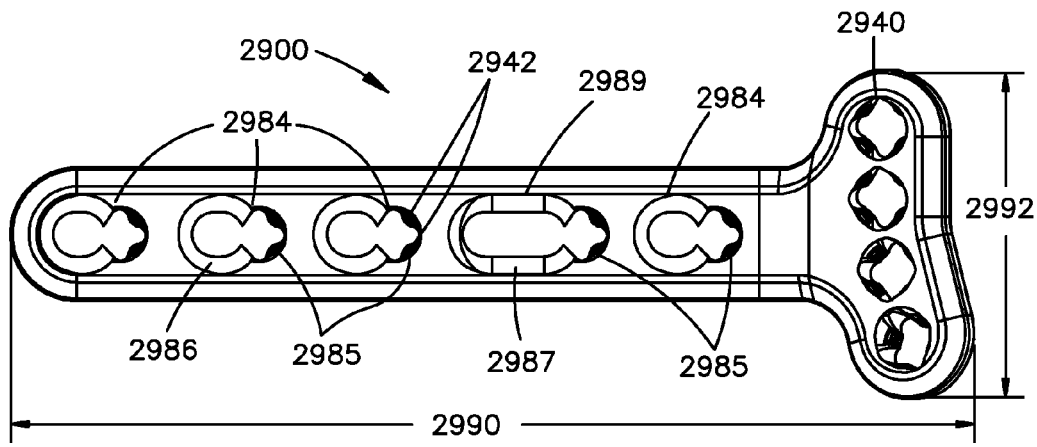

FIGS. 29A-C show another bone plate configuration in accordance with the invention (this is same bone plate shown in FIGS. 25-27). Bone plate 2900 is shaped and configured for, but not limited to, fractures of the distal radius. Bone plate 2900 has a head portion 2980 configured and dimensioned to conform to the metaphysis of the distal radius, and a shaft portion 2982 configured and dimensioned to conform to a diaphysis of the distal radius. Bone plate 2900 further has an upper surface 2937, a lower surface 2939, and a plurality of bone plate holes 2940 that extend completely through the bone plate, from upper surface 2937 to lower surface 2939. Each hole 2940 has preferably four columns of thread segments 2942 and can advantageously receive either a non-locking, locking, or variable-angle locking bone screw according to the invention. Shaft portion 2982 also has several combination holes 2984 and 2989 for increased versatility. Hole portions 2985 of the combination holes have preferably four columns of thread segments 2942 and the other portions 2886 and 2887 are preferably smooth and unthreaded. Portions 2886 and 2887 can receive a non-locking bone screw, while portions 2885 can advantageously receive either a non-locking, locking, or variable-angle locking bone screw. In one embodiment, the length 2990 of bone plate 2900 is about 65 mm, the width 2992 of head portion 2980 is about 22.2 mm, and the angle 2994 at which head portion 2980 is inclined upward with respect to shaft portion 2982 is about 25 degrees.

As shown in FIG. 30, bone plates of the invention preferably may be shaped to limit and/or minimize contact between the lower surface or underside of the bone plate and the bone. Limiting and/or minimizing contact between the bone plate and bone has a number of biological and mechanical advantages including reduced damage to blood supply and easier plate removal. One way to limit and/or minimize contact between a bone plate 3000 and bone is to provide plate 3000 with radiused or scalloped cutouts 3099 on lower surface 3039 between bone plate holes. Other ways are disclosed in U.S. Pat. Nos. 5,151,103; 5,053,036; 5,002,544; and 4,838,252. The contents of these patents are incorporated herein by reference.

FIG. 31 shows an embodiment of the bone plate system of the invention as applied to a bone fracture. Bone plate 2900 is shown attached to fractured bone 3178 via four variable-angle locking screws 3160 inserted at various selectable angles through bone plate holes 2940 of head portion 2980 and attached to bone plate 2900 via the columns of thread segments in holes 2940. The columns of thread segments on the inner surface of bone plate holes 2940 interact and mate with the thread on the spherically-shaped head of variable-angle locking screws 360 generally analogous to a rack-and-pinion, allowing the variable-angle screws 3160 to be secured in plate holes 2940 at a variety of angles. Variable-angle locking screws 3160 are constructed in accordance with the invention and may be, for example, variable-angle locking screws 500, 600, and/or 700. Bone plate 2900 is also attached to bone 3178 via non-locking bone screw 31100 inserted through portion 2987 of bone plate hole 2989. Bone plate 2900 is further attached to bone 3178 via a pair of conventional locking bone screws 31200 inserted through respective portions 2985 of bone plate holes 2984 and secured to the bone plate via the columns of thread segments in portion 2985. The columns of thread segments in the bone plate holes mate with the threaded heads of the locking screws to secure the locking screws to the bone plate. Note that variable-angle locking screws of the invention could have been used in place of locking screws 31200. Note further that not all bone plate holes need to be used in each application. Variable-angle locking screws 3160, non-locking screw 31100, and locking screws 31200 remain inserted through bone plate 2900 and into bone 3178 for as long as plate 2900 remains implanted.

Figure 32:
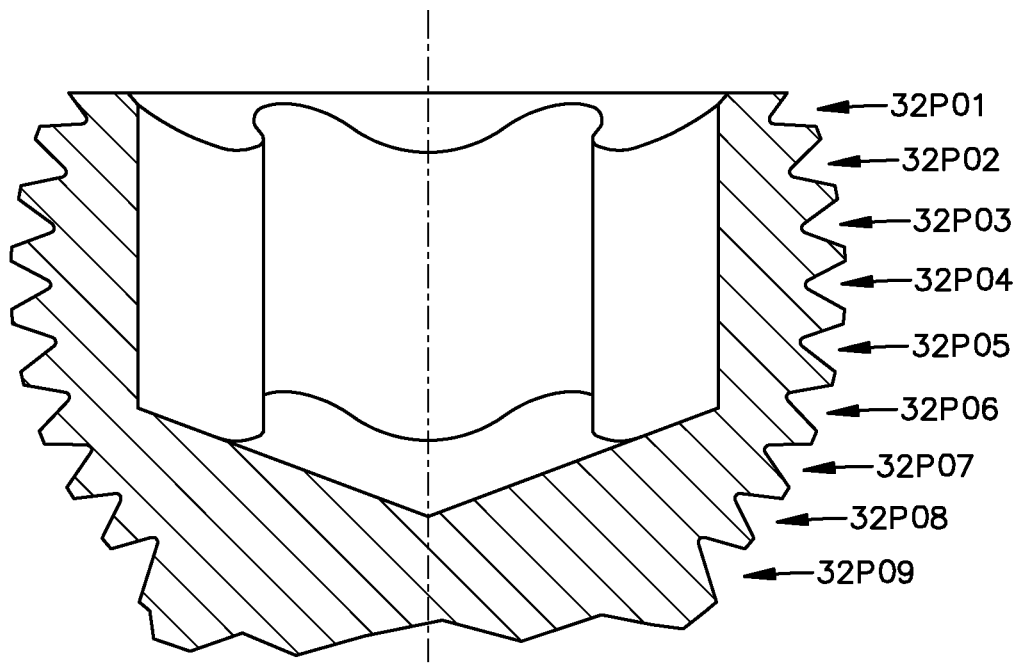
FIGS. 32-34 are cross-sectional views of three respective embodiments of a screwhead of a variable-angle locking bone screw according to the invention.
Figure 33:
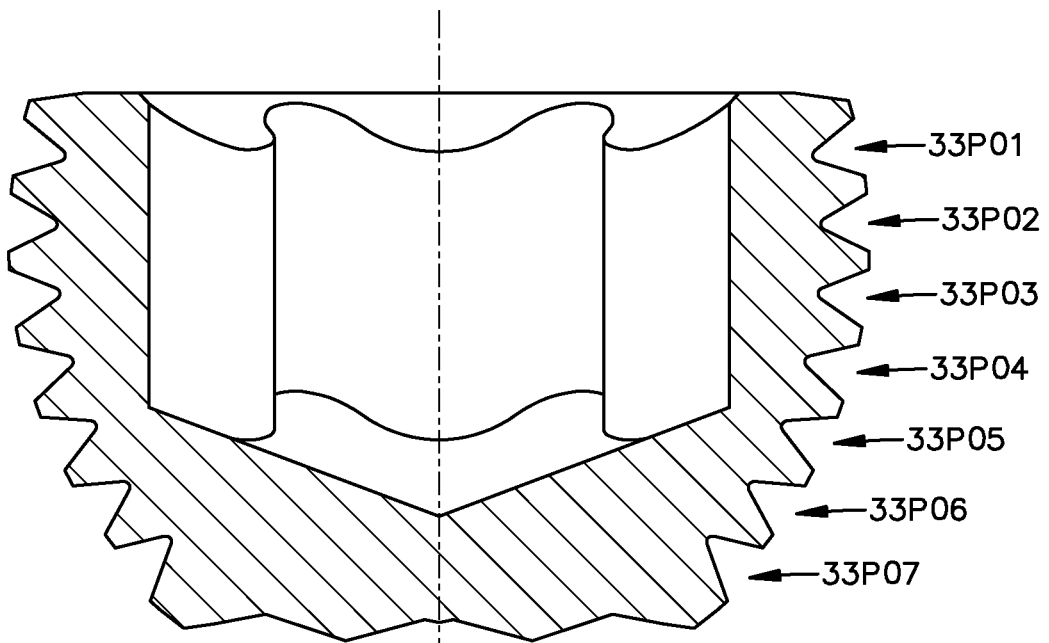
Figure 34:
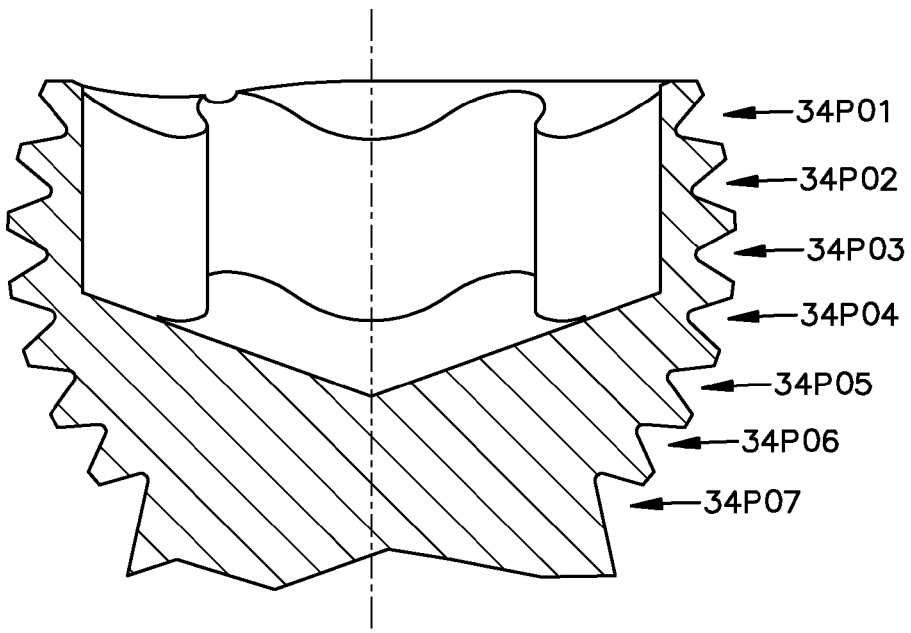

Returning to the screwhead thread features of variable-angle locking bone screws constructed in accordance with the invention, FIGS. 32-34 show three embodiments of a variable-angle locking screw screwhead that illustrate the varying thread pitches (e.g., the peak to peak distance) as measured along the central axis of each screw. The following table lists the size of the variable-angle screw to which the illustrated screwhead belongs and the varying pitches (all dimensions in millimeters).

|  | FIG. 32 | FIG. 33 | FIG. 34 |
|---|---|---|---|
| Shaft diameter: | 5.0 | 3.5 | 2.4 |
| Screwhead diameter: | 6.5 | 4.5 | 3.0 |
| Pitch: | 32P01 = 0.90 | 33P01 = 0.76 | 34P01 = 0.56 |
|  | 32P02 = 0.95 | 33P02 = 0.79 | 34P02 = 0.59 |
|  | 32P03 = 0.99 | 33P03 = 0.80 | 34P03 = 0.60 |
|  | 32P04 = 1.00 | 33P04 = 0.79 | 34P04 = 0.58 |
|  | 32P05 = 0.99 | 33P05 = 0.75 | 34P05 = 0.55 |
|  | 32P06 = 0.95 | 33P06 = 0.68 | 34P06 = 0.49 |
|  | 32P07 = 0.90 | 33P07 = 0.60 | 34P07 = 0.41 |
|  | 32P08 = 0.82 |  |  |
|  | 32P09 = 0.72 |  |  |

Other embodiments of variable-angle locking bone screws of the invention may have other varying thread pitches.

Figure 35:
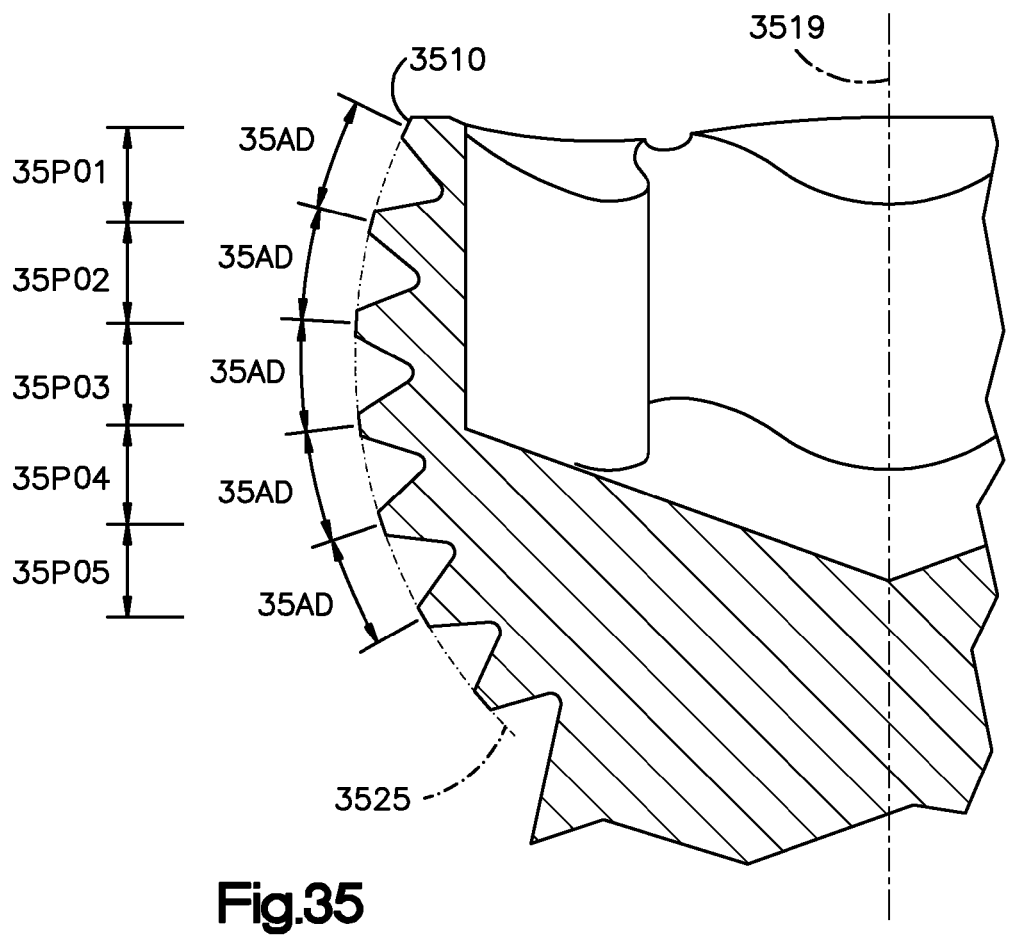
FIG. 35 is an enlarged partial cross-sectional view of a screwhead of a variable-angle locking bone screw according to the invention.

Note that in each case, the angular distance between adjacent thread peaks (or adjacent thread troughs) as measured along the radius of curvature is constant, as illustrated in FIG. 35. That is, each angular distance 35AD between adjacent thread peaks 3510 as measured along the radius of curvature 3525 is the same—in contrast to thread pitches 35P01-35P05 which, as illustrated in FIGS. 32-34, vary as measured along or parallel to central axis 3519.

By combining variable-angle locking screws, locking screws, and non-locking screws on the same bone plate using the same type of bone plate hole, the invention provides a novel mixed fixation. With non-locking screws, fracture reduction is held by friction between the bone plate and bone. This friction is generated by tightening the non-locking screws in bone. However, micromotion between the non-locking screws and bone leads to bone resorption and consequently loss of reduction. Additionally, insertion of the non-locking screws requires bone to withstand the stresses of screw tightening, which creates high stress in bone surrounding the non-locking screws. Ordinarily, the high stress can cause the non-locking screw threads to strip (i.e., threads in bone fail in shear) and/or creep in bone (since bone is a viscoelastic material). Either one of these phenomenon also results in loss of reduction.

By adding at least one locking or variable-angle locking screw, loss of reduction is minimized or eliminated. Specifically, by securing the locking screws to the bone plate and not the bone, the effect of the viscoelastic behavior of bone is reduced, the threads do not strip, and micromotion is prevented. The attachment between the locking screws and the bone plate is a high strength connection of fixed angle construct in which the locking screw has to cut sideways through the bone to fail.

Using variable-angle screws provides an even greater advantage than the locking screws, because the variable-angle screws may be secured at a more desirable angle than the locking screws.

Moreover, as management of certain peri-articular fractures typically involves insertion of screws at various angles with respect to the bone plate, and in view of the importance of maintaining the initial angular relationships between the individual screws and the plate, the highly-versatile bone plate system of the invention is particularly well-suited for these clinical applications.

Note that the features described and illustrated herein may be used singularly or in combination with other features and embodiments of bone plate systems.

The invention has thus been described above in connection with the preferred embodiments. The invention is not, however, limited to these embodiments, which are only examples of the invention. Persons skilled in the art will appreciate that various modifications can be made within the scope of the invention, and the invention is limited only by the claims which follow.

What is claimed:

1. A bone screw that is elongate along a direction, the bone screw including a central axis that is parallel to the direction, the bone screw comprising:
   a head including an outer surface, the head having a thread on the outer surface, the thread having a cross-sectional profile comprising a first plurality of peaks that each lie on a non-linear curve, a first plurality of troughs that each are positioned between adjacent ones of the first plurality of peaks, and a first plurality of flanks that each connect one of the first plurality of peaks to an adjacent one of the first plurality of troughs, the cross-sectional profile further comprising a second plurality of peaks that are opposite the first plurality of peaks with respect to the central axis, and a second plurality of troughs that are opposite the first plurality of troughs with respect to the central axis, each of the second plurality of troughs positioned between adjacent ones of the second plurality of peaks;
   a threaded shaft that extends from the head along the central axis, the threaded shaft configured and dimensioned to engage a bone;
   wherein the head defines a plurality of trough profile lines, each of the plurality of trough profile lines being a straight line perpendicular to the central axis, intersects opposed ones of the first and second pluralities of troughs, and is parallel to others of the plurality of the trough profile lines, and
   wherein adjacent ones of the first plurality of troughs are separated by respective thread trough-to-trough distances as measured along the direction, the respective thread trough-to-trough distances being configured to mate with a plurality of columns of protrusions arranged on an inner surface of a hole of a bone plate so as to lock the bone screw relative to the hole at a selectable angle within a range of angles at which the bone screw can mate and lock to the bone plate.

2. The bone screw of claim 1, wherein the bone screw defines a thread pitch defined as the distance between adjacent ones of the first plurality of peaks as measured along the central axis.

3. The bone screw of claim 2, wherein the thread pitch between a first pair of the first plurality of peaks is different than the thread pitch between a second pair of the first plurality of peaks.

4. The bone screw of claim 1, wherein the non-linear curve defines a radius of curvature that has a center.

5. The bone screw of claim 4, wherein the center lies on the central axis.

6. The bone screw of claim 4, wherein the center is spaced a distance away from the central axis with respect to a direction perpendicular to the central axis, the distance being greater than zero.

7. The bone screw of claim 4, wherein the non-linear curve forms a portion of a circle.

8. The bone screw of claim 1, wherein the head is partially spherically-shaped.

9. The bone screw of claim 1, wherein the non-linear curve is a first non-linear curve, and the first plurality of troughs lie on a second non-linear curve.

10. The bone screw of claim 9, wherein the second non-linear curve forms a portion of a circle.

11. The bone screw of claim 9, wherein the first and second non-linear curves are parallel.

12. The bone screw of claim 1, wherein each of the plurality of trough profile lines normally intersects the one of the first plurality of troughs and the one of the second plurality of troughs.

13. The bone screw of claim 1, wherein each of the plurality of trough profile lines bisects the opposed ones of the first and second pluralities of troughs.

14. The bone screw of claim 1, wherein each of the first plurality of troughs is spaced from the central axis by a distance that is less than the distance the adjacent ones of the first plurality of peaks is spaced from the central axis.

15. A bone screw that is elongate along a direction, the bone screw comprising:
   a head including an outer surface, the head having a thread on the outer surface, the thread having a cross-sectional profile comprising a plurality of peaks that each lie on a non-linear curve, a plurality of troughs each of which are positioned between adjacent ones of the plurality of peaks, and a plurality of flanks each of which connect one of the plurality of peaks to an adjacent one of the plurality of troughs; and
   a threaded shaft that extends from the head along a central axis that is parallel to the direction, the threaded shaft configured and dimensioned to engage a bone;
   wherein the plurality of troughs includes a first pair of adjacent troughs, a second pair of adjacent troughs, and a third pair of adjacent troughs, at least one of the troughs of the third pair of adjacent troughs positioned closer to the threaded shaft with respect to the direction than both of the troughs of the second pair of adjacent troughs are from the threaded shaft with respect to the direction, at least one of the troughs of the second pair of adjacent troughs positioned closer to the threaded shaft with respect to the direction than both of the troughs of the first pair of adjacent troughs are from the threaded shaft with respect to the direction,
   wherein the bone screw defines a thread pitch defined as the offset between adjacent ones of the plurality of troughs as measured along the direction, and the thread pitch between the troughs of the first pair of adjacent troughs is less than the thread pitch between the troughs of the second pair of adjacent troughs, and the thread pitch between the troughs of the second pair of adjacent troughs is greater than the thread pitch between the troughs of the third pair of adjacent troughs.

16. The bone screw of claim 15, wherein the non-linear curve defines a radius of curvature that has a center, and the center lies on the central axis.

17. The bone screw of claim 15, wherein the non-linear curve defines a radius of curvature that has a center, and the center is spaced a distance away from the central axis with respect to a direction perpendicular to the central axis, the distance being greater than zero.

18. The bone screw of claim 15, wherein the non-linear curve is a first non-linear curve, and the first plurality of troughs lie on a second non-linear curve.

19. The bone screw of claim 18, wherein the first and second non-linear curves are parallel to each other.

* * * * *